US006015823A

United States Patent [19]

Krämer et al.

[11] Patent Number: 6,015,823

[45] Date of Patent: Jan. 18, 2000

[54] 4-CYCLOHEXYLPHENYL-OXAZOLINES AND THEIR USE FOR CONTROLLING ANIMAL PESTS

[75] Inventors: Wolfgang Krämer, Burscheid; Christoph Erdelen, Leichlingen; Ulrike Wachendorff-Neumann, Neuwied; Andreas Turberg, Haan; Norbert Mencke, Leverkusen, all of Germany

[73] Assignee: Bayer Aktiengesellschaft, Leverkusen, Germany

[21] Appl. No.: 09/308,621

[22] PCT Filed: Nov. 17, 1997

[86] PCT No.: PCT/EP97/06392

§ 371 Date: May 19, 1999

§ 102(e) Date: May 19, 1999

[87] PCT Pub. No.: WO98/23600

PCT Pub. Date: Jun. 4, 1998

[30] Foreign Application Priority Data

Nov. 28, 1996 [DE] Germany .......................... 196 49 307

[51] Int. Cl.[7] ........................ A01N 43/76; C07D 263/10; C07D 263/14; C07D 263/52; C07D 413/10

[52] U.S. Cl. .......................... 514/374; 548/216; 548/239

[58] Field of Search .................................... 548/239, 216; 514/374

[56] References Cited

U.S. PATENT DOCUMENTS

| | | | |
|---|---|---|---|
| 5,141,948 | 8/1992 | Miyamoto et al. | 514/365 |
| 5,354,905 | 10/1994 | Sato et al. | 564/186 |
| 5,578,625 | 11/1996 | Suzuki et al. | 514/374 |

FOREIGN PATENT DOCUMENTS

| | | |
|---|---|---|
| 95-14548 | 8/1995 | Australia . |
| 2155821 | 2/1996 | Canada . |
| 94/29268 | 12/1994 | WIPO . |

*Primary Examiner*—Laura L. Stockton
*Attorney, Agent, or Firm*—Joseph C. Gil; Carol Marmo

[57] ABSTRACT

The present invention relates to novel 4-cyclohexylphenyl-oxazolines of the formula (I)

(I)

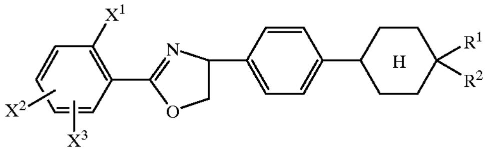

in which $X^1$, $X^2$, $X^3$, $R^1$ and $R^2$ are each as defined in the description, to processes for their preparation and to their use for controlling animal pests.

25 Claims, No Drawings

4-CYCLOHEXYLPHENYL-OXAZOLINES AND THEIR USE FOR CONTROLLING ANIMAL PESTS

This application is a 371 of PCT/EP97/06392 filed Nov. 17, 1997.

TECHNICAL FIELD OF THE INVENTION

The present invention relates to novel 4-cyclohexylphenyl-oxazolines, to a process for their preparation and to their use for controlling animal pests.

BACKGROUND OF THE INVENTION

It is already known that certain substituted biphenyl-oxazolines have insecticidal and acaricidal properties (cf. for example EP-A-0 432 661 or EP-A-0 696 584). However, the efficacy and/or the duration of action of these known compounds, in particular against certain organisms or at low application concentrations, is not entirely satisfactory in all areas of application.

DETAILED DESCRIPTION OF THE INVENTION

This invention, accordingly, provides novel 4-cyclohexylphenyl-oxazolines of the formula (I)

(I)

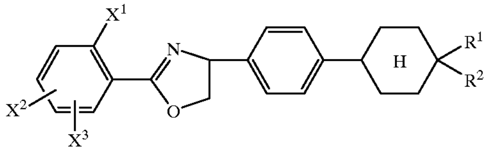

in which $X^1$ represents halogen, alkyl, alkoxy, alkylthio, halogenoalkyl, halogenoalkoxy, amino, alkylamino or dialkylamino, $X^2$ and $X^3$ are identical or different and each represents hydrogen, halogen, alkyl, alkoxy, alkylthio, halogenoalkyl, halogenoalkoxy, amino, alkylamino or dialkylamino, $R^1$ represents hydrogen, —$OR^3$ or —$SR^3$ and $R^2$ represents —$OR^4$, where $R^3$ and $R^4$ are identical or different and each represents hydrogen, alkyl, alkenyl or optionally substituted benzyl, or they join with the hetero atoms to which they are attached and the carbon atom linking these to form an optionally substituted 5- or 6-membered ring;

or $R^1$ and $R^2$ together represent oxygen or represent =N—$OR^5$ or =—$NR^6R^7$, where $R^5$ represents hydrogen, alkyl, alkenyl, alkynyl, halogenoalkyl or optionally substituted benzyl;

$R^6$ represents hydrogen, alkyl, alkenyl, alkynyl, halogenoalkyl or optionally substituted benzyl; and $R^7$ represents alkyl, alkylcarbonyl, alkoxycarbonyl, respectively optionally substituted phenyl, phenylcarbonyl or benzyl or represents —$CONR^8R^9$ or —$SO_2NR^8R^9$ in which $R^8$ represents hydrogen, alkyl, alkenyl, alkynyl, halogenoalkyl or optionally substituted benzyl and $R^9$ represents alkyl, alkylcarbonyl, alkoxycarbonyl or respectively optionally substituted phenyl, phenylcarbonyl or benzyl.

The 4-cyclohexylphenyl-oxazolines of the formula (1) can be present as optical and/or geometrical isomers, which depends, among other things, on the substituents. The present invention provides the isomer mixtures, and also the pure isomers.

Furthermore, it was found that the 4-cyclohexylphenyl-oxazolines of the formula (I) are obtained when a) chloroethane derivatives of the formula (II)

(II)

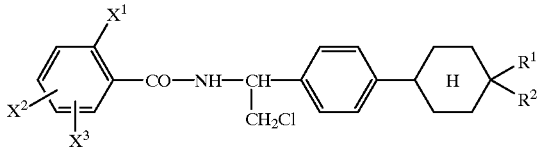

in which $X^1$, $X^2$, $X^3$, $R^1$ and $R^2$ are each as defined above, are cyclized in the presence of a base, if appropriate in the presence of a catalyst and if appropriate in the presence of a diluent;

or b) 4-cyclohexylphenyl-oxazolines of the formula (Ia)

(Ia)

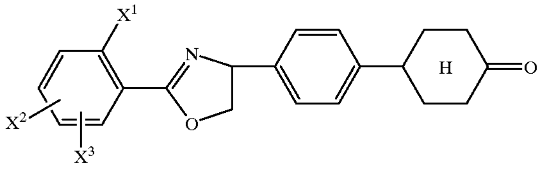

which are obtainable by the process (a) and in which $X^1$, $X^2$ and $X^3$ are each as defined above, are derivatized in a conventional and generally known manner to give (b1) ketals by reaction with alcohols of the formula (III), thioalcohols of the formula (IV) or compounds of the formula (V)

$HOR^{10}$ (III)

$HSR^{10}$ (IV)

HO—A—O(S)H (V)

in which $R^{10}$ has the abovementioned meanings of $R^3$ and/or $R^4$ and

A represents an optionally substituted $C_2$- or $C_3$-hydrocarbon chain, if appropriate in the presence of a catalyst and if appropriate in the presence of a diluent;

or (b2) oximes and oxime ethers by reaction with hydroxylamines of the formula (VI)

$H_2N—O—R^5$ (VI)

in which $R^5$ is as defined above or with salts thereof such as, for example, hydrogen halide adducts, if appropriate in the presence of a diluent and if appropriate in the presence of a base; it is also possible to alkylate the resulting derivatives where $R^5$=hydrogen subsequently;

or (b3) hydrazones by reaction with hydrazines of the formula (VII)

$H_2N—NR^6R^7$ (VII)

in which $R^6$ and $R^7$ are each as defined above, if appropriate in the presence of a diluent;

or c) 4-cyclohexylphenyl-oxazolines of the formula (Ib)

(Ib)

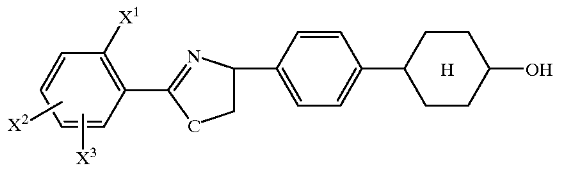

which are obtainable by process (a) and in which $X^1$, $X^2$ and $X^3$ are each as defined above, are reacted with halides of the formula (VIII)

$R^{11}$—Hal (VIII)

in which $R^{11}$ represents alkyl or optionally substituted benzyl and

Hal represents halogen, in the presence of a base and if appropriate in the presence of a diluent.

Furthermore, it was found that the novel 4-cyclohexylphenyl-oxazolines of the formula (I) are highly suitable for controlling animal pests, in particular insects, arachnids and nematodes, encountered in agriculture, in forestry, in the protection of stored products and of materials, and in the hygiene sector.

The formula (I) provides a general definition of the compounds according to the invention.

Preferred substituents or ranges of the radicals listed in the formulae mentioned hereinabove and hereinbelow are illustrated below.

$X^1$ preferably represents fluorine, chlorine, bromine, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, amino, $C_1$–$C_4$-alkylamino or di($C_1$–$C_4$-alkyl)amino (in particular fluorine or chlorine, especially fluorine).

$X^2$ and $X^3$ are identical or different and each preferably represents hydrogen, fluorine, chlorine, bromine, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, amino, $C_1$–$C_4$-alkylamino or di($C_1$–$C_4$-alkyl)amino (where $X^3$ in particular represents hydrogen and $X^2$ in particular represents fluorine or chlorine, especially fluorine, in each case preferably in position 6).

$R^1$ preferably represents hydrogen, —$OR^3$ or —$SR^3$ and $R^2$ preferably represents the radical —$OR^4$, or $R^1$ and $R^2$ together preferably represent oxygen, preferably represent =N—$OR^5$ or =N—$NR^6R^7$.

$R^3$ and $R^4$ are identical or different and each preferably represents hydrogen, $C_1$–$C_4$-alkyl or benzyl which is optionally mono- to trisubstituted, preferably in the phenyl moiety, by identical or different substituents from the group consisting of halogen, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, cyano, nitro, di($C_1$–$C_4$-alkyl)amino and $C_1$–$C_4$-alkoxycarbonyl or they join with the hetero atoms to which they are attached and the carbon atom linking these to form a 5- or 6-membered ring (preferably not containing any further hetero atoms) which is optionally mono- or disubstituted by identical or different substitutents, suitable substituents being $C_1$–$C_{18}$-alkyl which is optionally substituted by halogen, $C_1$–$C_6$-alkoxy, $C_2$-$C_6$-alkenyloxy, benzyloxy or phenoxy (each of which is optionally mono- to trisubstituted, preferably mono- or disubstituted, in the ring, by identical or different substituents from the group consisting of halogen, $C_1$–C8-alkyl, $C_1$–$C_4$-alkoxy and phenoxy), $C_2$-$C_6$-alkenyl, phenyl which is optionally mono- to trisubstituted by identical or different substituents from the group consisting of halogen, $C_1$–$C_4$-alkyl, $C_1$–$C_4$-alkoxy, $C_1$-$C_4$-alkylthio, $C_1$–$C_4$-halogenoalkyl, $C_1$–$C_4$-halogenoalkoxy, $C_1$–$C_4$-halogenoalkylthio, cyano, nitro, di($C_1$–$C_4$-alkyl)amino, $C_1$–$C_4$-alkoxycarbonyl, phenyl (which is optionally mono- or disubstituted by identical or different substituents from the group consisting of halogen and $C_1$–$C_4$-alkyl) and benzyloxy (which is optionally mono- or disubstituted in the ring by identical or different substituents from the group consisting of halogen and $C_1$–$C_4$-alkyl) and —$NR^{12}R^{13}$.

$R^{12}$ preferably represents hydrogen, $C_1$–$C_4$-alkyl, $C_2$-$C_4$-alkenyl, $C_2$-$C_4$-alkynyl, $C_1$–$C_4$-halogenoalkyl or benzyl which is optionally mono- to trisubstituted, preferably in the phenyl moiety, by identical or different substituents from the group consisting of halogen, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, cyano, nitro, di($C_1$–$C_4$-alkyl)amino and $C_1$–$C_4$-alkoxycarbonyl.

$R^{13}$ preferably represents $C_1$–$C_4$-alkyl, $C_1$–$C_4$-alkylcarbonyl, $C_1$–$C_4$-alkoxyl-carbonyl, represents phenyl, phenylcarbonyl or benzyl, each of which is optionally mono- to trisubstituted, preferably in the phenyl moiety, by identical or different substituents from the group consisting of halogen, $C_1$–$C_4$-alkyl, $C_1$–$C_4$-alkoxy, $C_1$–$C_4$-alkylthio, $C_1$–$C_4$-halogenoalkyl, $C_1$–$C_4$ -halogenoalkoxy, $C_1$–$C_4$-halogenoalkylthio, cyano, nitro, di($C_1$–$C_4$-alkyl) amino and $C_1$–$C_4$-alkoxy-carbonyl, represents —$CONR^{14}R^{15}$ or —$SO_2NR^{14}R^{15}$.

$R^{14}$ preferably represents hydrogen, $C_1$–$C_4$-alkyl, $C_2$–$C_4$-alkenyl, $C_2$–$C_4$-alkynyl, $C_1$–$C_4$-halogenoalkyl or benzyl which is optionally mono- to trisubstituted, preferably in the phenyl moiety, by identical or different substituents from the group consisting of halogen, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, cyano, nitro, di($C_1$–$C_4$-alkyl)amino or $C_1$–$C_4$-alkoxycarbonyl.

$R^{15}$ preferably represents $C_1$–$C_4$-alkyl, $C_1$–$C_4$-alkyl-carbonyl, $C_1$–$C_4$-alkoxy-carbonyl, represents phenyl, phenylcarbonyl or benzyl, each of which is optionally mono- to trisubstituted, preferably in the phenyl moiety, by identical or different substituents from the group consisting of halogen, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, cyano, nitro, di($C_1$–$C_4$-alkyl) amino or $C_1$–$C_4$-alkoxy-carbonyl, $R^5$ preferably represents hydrogen, $C_1$–$C_6$-alkyl, $C_2$–$C_6$-alkenyl, $C_2$–$C_6$-alkynyl, $C_1$–$C_4$-halogenoalkyl or benzyl which is optionally mono- to trisubstituted, preferably in the phenyl moiety, by identical or different substituents from the group consisting of halogen, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, cyano, nitro, di($C_1$–$C_4$-alkyl)amino or $C_1$–$C_4$-alkoxy-carbonyl.

$R^6$ preferably represents hydrogen, $C_1$–$C_4$-alkyl, $C_2$–$C_4$-alkenyl, $C_1$–$C_4$-alkynyl, $C_1$–$C_4$-halogenoalkyl or benzyl which is optionally mono- to trisubstituted, preferably in the phenyl moiety, by identical or different substituents from the group consisting of halogen, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, cyano, nitro, di($C_1$–$C_4$-alkyl)amino or $C_1$–$C_4$-alkoxy-carbonyl.

$R^7$ preferably represents $C_1$–$C_4$-alkyl, $C_1$–$C_4$-alkyl-carbonyl, $C_1$–$C_4$-alkoxy-carbonyl, represents phenyl, phenylcarbonyl or benzyl, each of which is optionally mono- to trisubstituted, preferably in the phenyl moiety, by identical or different substituents from the group consisting of halogen, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, cyano, nitro, di($C_1$–$C_4$-alkyl)amino or $C_1$–$C_4$-alkoxy-carbonyl, or represents —$CONR^8R^9$ or —$SO_2NR^8R^9$.

$R^8$ preferably represents hydrogen, $C_1$–$C_4$-alkyl, $C_2$–$C_4$-alkenyl, $C_2$–$C_4$-alkynyl, $C_1$–$C_4$-halogenoalkyl or benzyl which is optionally mono- to trisubstituted, preferably in the phenyl moiety, by identical or different substituents from the group consisting of halogen, $C_1$–$C_4$-alkyl, $C_1$-$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, cyano, nitro, di($C_1$–$C_4$-alkyl)amino or $C_1$–$C_4$-alkoxy-carbonyl.

$R^9$ preferably represents $C_1$–$C_4$-alkyl, $C_1$–$C_4$-alkyl-carbonyl, C -$C_4$-alkoxy-carbonyl, represents phenyl, phenylcarbonyl or benzyl, each of which is optionally mono- to trisubstituted, preferably in the phenyl moiety, by identical or different substituents from the group consisting of halogen, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, cyano, nitro, di($C_1$–$C_4$-alkyl)amino or $C_1$–$C_4$-alkoxy-carbonyl.

$X^1$ particularly preferably represents fluorine, chlorine or methyl, (in particular fluorine or chlorine, especially fluorine).

$X^2$ and $X^3$ are identical or different and each particularly preferably represents hydrogen, represents fluorine, chlorine, methyl, ethyl, methoxy, methylthio, trifluoromethyl, trifluoromethoxy, amino, dimethylamino or diethylamino, (where $X^3$ in particular represents hydrogen and $X^2$ in particular represents fluorine or chlorine, especially fluorine, in each case preferably in position 6).

$R^1$ particularly preferably represents hydrogen, —$OR^3$ or —$SR^3$ and $R^2$ particularly preferably represents the radical —$OR^4$, or $R^1$ and $R^2$ together particularly preferably represent oxygen, represent =N—$OR^5$ or =N—$NR^6R^7$.

$R^3$ and $R^4$ are identical or different and each particularly preferably represents hydrogen, methyl, ethyl, n- or i-propyl, n-, i-, s- or t-butyl; or represent benzyl which is optionally mono- or disubstituted, preferably in the phenyl moiety, by identical or different substituents from the group consisting of fluorine, chlorine, bromine, methyl, ethyl, n- or i-propyl, n-, i-, s- or t-butyl; methoxy, ethoxy, methylthio, trifluoromethyl, trifluoromethoxy, trifluoromethylthio, cyano, nitro, dimethylamino, diethylamino, methoxycarbonyl or ethoxycarbonyl, or they join with the hetero atoms to which they are attached and the carbon atom linking these to form a 5- or 6-membered ring (preferably not containing any further hetero atoms) which is optionally mono- to trisubstituted, preferably mono- or disubstituted, by identical or different substituents, suitable substituents being $C_1$–$C_{18}$-alkyl which is optionally substituted by fluorine, chlorine, methoxy, ethoxy, n- or i-propoxy, n-butyloxy, allyloxy, benzyloxy (which is in each case optionally mono- to trisubstituted, preferably mono- or disubstituted, in the ring, by identical or different substituents from the group consisting of fluorine, chlorine, bromine, methyl, ethyl, methoxy, ethoxy and phenoxy) and phenoxy, $C_2$–$C_4$-alkenyl, phenyl which is optionally mono- to trisubstituted by identical or different substituents from the group consisting of fluorine, chlorine, bromine, methyl, ethyl, n- or i-propyl, n-, i-, s- or t-butyl; methoxy, ethoxy, methylthio, trifluoromethyl, trifluoromethoxy, trifluoromethylthio, cyano, nitro, dimethylamino, diethylamino, methoxycarbonyl, ethoxycarbonyl, phenyl, halogenophenyl, benzyloxy and halogenobenzyloxy, and —$NR^{12}R^{13}$.

$R^{12}$ particularly preferably represents hydrogen, methyl, ethyl, n- or i-propyl, n-, i-, s- or t-butyl, allyl, propargyl, trifluoromethyl or represents benzyl which is optionally mono- to trisubstituted, preferably in the phenyl moiety, by identical or different substituents from the group consisting of fluorine, chlorine, bromine, methyl, ethyl, n- or i-propyl, n-, i-, s- or t-butyl; methoxy, ethoxy, methylthio, trifluoromethyl, trifluoromethoxy, trifluoromethylthio, cyano, nitro, dimethylamino, diethylamino, methoxycarbonyl and ethoxycarbonyl.

$R^{13}$ particularly preferably represents methyl, ethyl, n- or i-propyl, n-, i-, s- or t-butyl, methylcarbonyl, ethylcarbonyl, methoxycarbonyl, ethoxycarbonyl, represents phenyl, phenylcarbonyl or benzyl, each of which is optionally mono- or disubstituted, preferably in the phenyl moiety, by identical or different substituents from the group consisting of fluorine, chlorine, bromine, methyl, ethyl, n- or i-propyl, n-, i-, s- or t-butyl; methoxy, ethoxy, methylthio, trifluoromethyl, trifluoromethoxy, trifluoromethylthio, cyano, nitro, dimethylamino, diethylamino, methoxycarbonyl and ethoxycarbonyl, represents —$CONR^{14}R^{15}$ or —$SO_2NR^{14}R^{15}$.

$R^{14}$ particularly preferably represents hydrogen, methyl, ethyl, n- or i-propyl, n-, i-, s- or t-butyl, allyl, propargyl, trifluoromethyl or represents benzyl which is optionally mono- or disubstituted, preferably in the phenyl moiety, by identical or different substituents from the group consisting of fluorine, chlorine, bromine, methyl, ethyl, n- or i-propyl, n-, i-, s- or t-butyl; methoxy, ethoxy, methylthio, trifluoromethyl, trifluoromethoxy, trifluoromethylthio, cyano, nitro, dimethylamino, diethylamino, methoxycarbonyl and ethoxycarbonyl.

$R^{15}$ particularly preferably represents methyl, ethyl, n- or i-propyl, n-, i-, s- or t-butyl, methylcarbonyl, ethylcarbonyl, methoxycarbonyl, ethoxycarbonyl, represents phenyl, phenylcarbonyl or benzyl, each of which is optionally mono- or disubstituted, preferably in the phenyl moiety, by identical or different substituents from the group consisting of fluorine, chlorine, bromine, methyl, ethyl, n- or i-propyl, n-, i-, s- or t-butyl; methoxy, ethoxy, methylthio, trifluoromethyl, trifluoromethoxy, trifluoromethylthio, cyano, nitro, dimethylamino, diethylamino, methoxycarbonyl and ethoxycarbonyl.

$R^5$ particularly preferably represents hydrogen, methyl, ethyl, n- or i-propyl, n-, i-, s- or t-butyl, allyl, propargyl, trifluoromethyl or represents benzyl which is optionally mono- or disubstituted, preferably in the phenyl moiety, by identical or different substituents from the group consisting of fluorine, chlorine, bromine, methyl, ethyl, n- or i-propyl, n-, i-, s- or t-butyl; methoxy, ethoxy, methylthio, trifluoromethyl, trifluoromethoxy, trifluoromethylthio, cyano, nitro, dimethylamino, diethylamino, methoxycarbonyl and ethoxycarbonyl.

$R^6$ particularly preferably represents hydrogen, methyl, ethyl, n- or i-propyl, n-, i-, s- or t-butyl, allyl, propargyl, trifluoromethyl or represents benzyl which is optionally mono- or disubstituted, preferably in the phenyl moiety, by identical or different substituents from the group consisting of fluorine, chlorine, bromine, methyl, ethyl, n- or i-propyl, n-, i-, s- or t-butyl; methoxy, ethoxy, methylthio, trifluoromethyl, trifluoromethoxy, trifluoromethylthio, cyano, nitro, dimethylamino, diethylamino, methoxycarbonyl and ethoxycarbonyl.

$R^7$ particularly preferably represents methyl, ethyl, n- or i-propyl, n-, i-, s- or t-butyl, methylcarbonyl, ethylcarbonyl, methoxycarbonyl, ethoxycarbonyl, represents phenyl, phenylcarbonyl or benzyl, each of which is optionally mono- or disubstituted, preferably in the phenyl moiety, by identical or different substituents from the group consisting of fluorine, chlorine, bromine, methyl, ethyl, n- or i-propyl, n-, i-, s- or t-butyl; methoxy, ethoxy, methylthio, trifluoromethyl, trifluoromethoxy, trifluoromethylthio, cyano, nitro, dimethylamino, diethylamino, methoxycarbonyl and ethoxycarbonyl, or represents —$CONR^8R^9$ or —$SO_2NR^8R^9$.

$R^8$ particularly preferably represents hydrogen, methyl, ethyl, n- or i-propyl, n-, i-, s- or t-butyl, allyl, propargyl, trifluoromethyl or represents benzyl which is optionally mono- to trisubstituted, preferably in the phenyl moiety, by identical or different substituents from the group consisting of fluorine, chlorine, bromine, methyl, ethyl, n- or i-propyl, n-, i-, s- or t-butyl; methoxy, ethoxy, methylthio, trifluoromethyl, trifluoromethoxy, trifluoromethylthio, cyano, nitro, dimethylamino, diethylamino, methoxycarbonyl and ethoxycarbonyl.

$R^9$ particularly preferably represents methyl, ethyl, n- or i-propyl, n-, i-, s- or t-butyl, methylcarbonyl, ethylcarbonyl, methoxycarbonyl, ethoxycarbonyl, represents phenyl, phenylcarbonyl or benzyl, each of which is optionally mono- to disubstituted, preferably in the phenyl moiety, by identical or different substituents from the group consisting of fluorine, chlorine, bromine, methyl, ethyl, n- or i-propyl, n-, i-, s- or t-butyl; methoxy, ethoxy, methylthio, trifluoromethyl, trifluoromethoxy, trifluoromethylthio, cyano, nitro, dimethylamino, diethylamino, methoxycarbonyl and ethoxycarbonyl.

The abovementioned general or preferred definitions of radicals or illustrations apply to the end products and, correspondingly, to the starting materials and intermediates. These radical definitions can be combined with one another as desired, that is to say combinations between the respective preferred ranges are also possible.

Preference according to the invention is given to those compounds of the general formula (I) which contain a combination of the definitions given above as being preferred (preferable).

Particular preference according to the invention is given to those compounds of the general formula (1) which contain a combination of the definitions given above as being particularly preferred.

In the radical definitions mentioned hereinabove and hereinbelow, hydrocarbon radicals such as alkyl or alkenyl may be—also in connection with hetero atoms as in alkoxy or alkylthio—in each case straight-chain or branched as far as this is possible.

Preferred compounds according to the invention are substances of the formulae (IA) to (IE)

(IA)

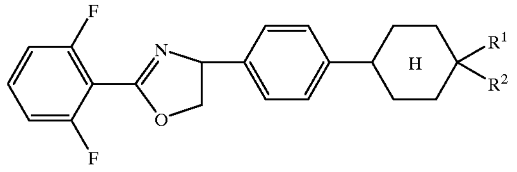

(IB)

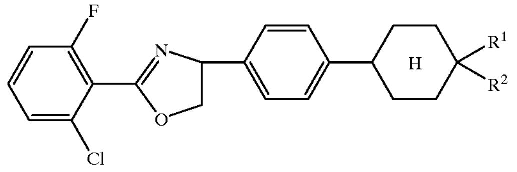

(IC)

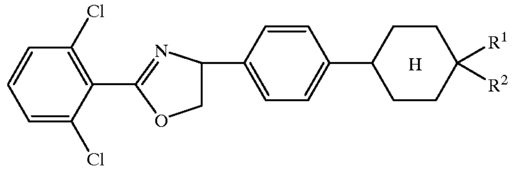

-continued (ID)

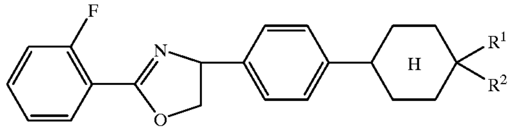

(IE)

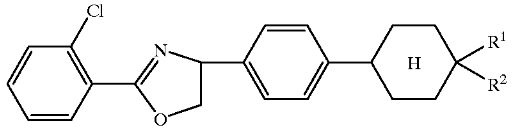

in which $R^1$ and $R^2$ are each as defined above.

Preferred compounds according to the invention are also substances of the formula (IF)

(IF)

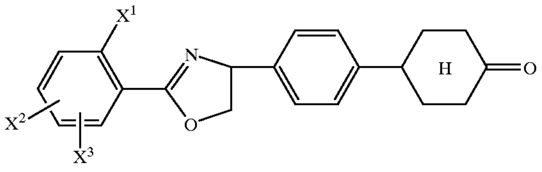

in which $X^1$, $X^2$ and $X^3$ are each as defined above.

Preferred compounds according to the invention are furthermore substances of the formula (1), i.e. also (IF), in which $X^1$ represents fluorine, chlorine, $C_1$–$C_2$-alkyl, $C_1$–$C_2$-alkoxy or $C_1$–$C_2$-alkylthio (in particular fluorine), $X^2$ represents hydrogen, fluorine or chlorine (in particular fluorine or chlorine, especially fluorine, very particularly 6-fluorine), $X^3$ represents hydrogen, fluorine, chlorine or $C_1$–$C_2$-alkyl (in particular hydrogen), $R^1$ represents the radical —$OR^3$ and $R^2$ represents the radical —$OR^4$ where $R^3$ and $R^4$ join with the oxygen atoms to which they are attached and the carbon atom linking these to form a five-membered ring (preferably not containing any further hetero atoms) which is optionally substituted by $C_1$–$C_{18}$-alkyl or phenyl which is optionally mono- to trisubstituted by identical or different substituents from the group consisting of halogen, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy and $C_1$–$C_4$-halogenoalkylthio.

Using, for example, 2-(2,6-difluorobenzoylamido-2-[4-(4-oxo-cyclohexyl)-phenyl]-1-chloroethane as starting material for carrying out the process (a) according to the invention, the course of the reaction may be illustrated by the following scheme:

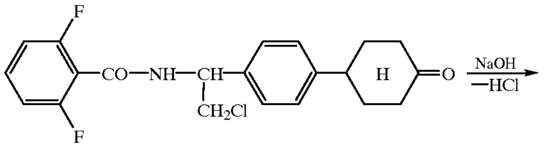

-continued

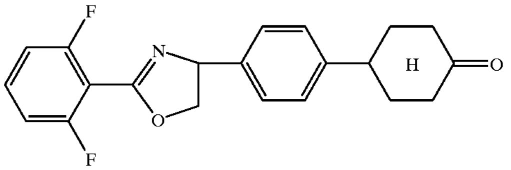

Using, for example, 2-(2,6-difluorophenyl-4-[4-(4-oxo-cyclohexyl)-phenyl]-1,3-oxazoline and (4-chlorophenyl)-ethane-1,2-diol as starting materials for carrying out the variant (b1) of the process (b) according to the invention, the course of the reaction may be illustrated by the following scheme:

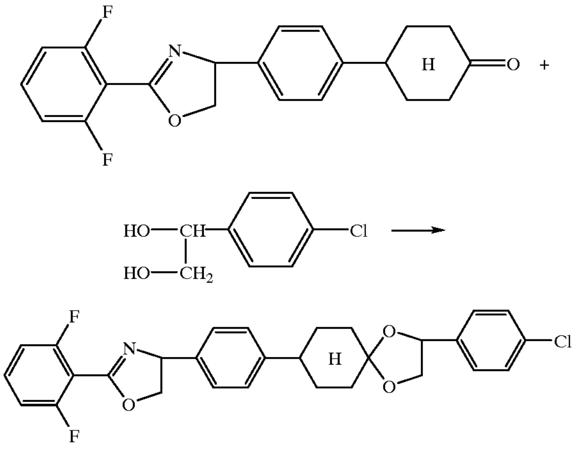

Using, for example, 2-(2,6-difluorophenyl)-4-[4-(4-oxo-cyclohexyl)-phenyl]-1,3-oxazoline and hydroxylamine hydrochloride as starting materials for carrying out the variant (b2) of the process (b) according to the invention, the course of the reaction may be illustrated by the following scheme:

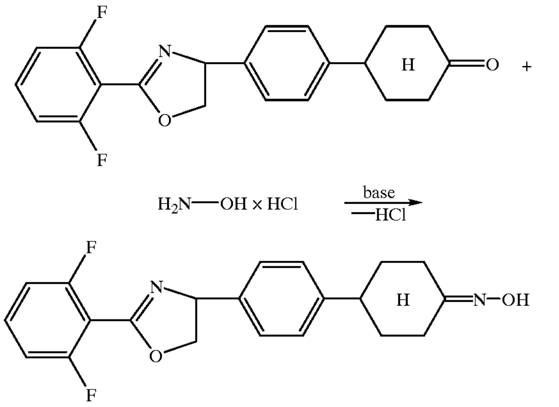

Using, for example, 2-(2,6-difluorophenyl)-4-[4-(4-oxo-cyclohexyl)-phenyl]-1,3-oxazoline and methylhydrazine as starting materials for carrying out the variant (b3) of the process (b) according to the invention, the course of the reaction may be illustrated by the following scheme:

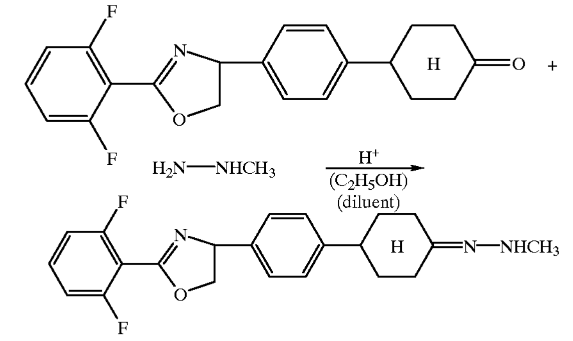

Using, for example, 2-(2,6-difluorophenyl)-4-[4-(4-hydroxycyclohexyl)-phenyl]-1,3-oxazoline and benzyl chloride as starting materials for carrying out the process (c) according to the invention, the course of the reaction may be illustrated by the following scheme:

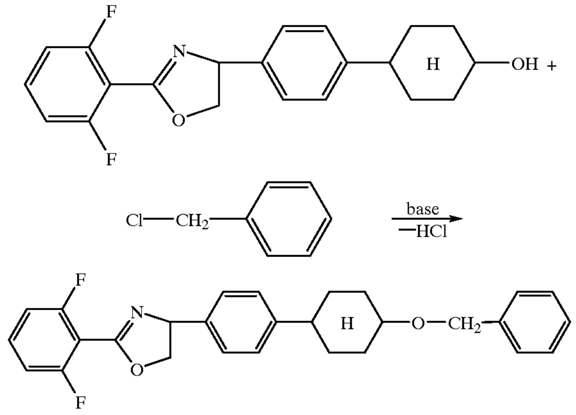

The chloroethane derivatives of the formula (II) to be used as starting materials in the process (a) according to the invention are novel.

They are obtained, for example, by reacting amide derivatives of the formula (IX)

(IX)

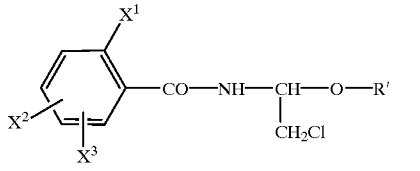

in which $X^1$, $X^2$ and $X^3$ are each as defined above and

R' represents $C_1$–$C_4$-alkyl, preferably methyl or ethyl, with phenyl derivatives of the formula (X)

(X)

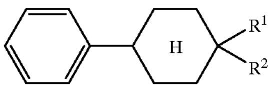

in which $R^1$ and $R^2$ are each as defined above, in the presence of an acid catalyst and in the presence of a diluent.

Suitable diluents are all solvents which are inert to the reaction participants.

Preference is given to hydrocarbons, such as hexane, halogenated hydrocarbons, such as methylene chloride, chloroform, chlorobenzene, o-dichlorobenzene; and to carbon disulphide.

Suitable acid catalysts are in principle all inorganic or organic acids or Lewis acids. Preference is given to using, for example, sulphuric acid, methanesulphonic acid, benzensulphonic acid, anhydrous hydrofluoric acid, aluminium chloride, titanium tetrachloride, phosphorus oxychloride, boron trifluoride etherate. If appropriate, an excess of acid may also serve as diluent.

The reaction temperature can be varied within a relatively wide range. In general, the reaction is carried out at temperatures between −20° C. and 150° C., preferably between −20° C. and +20° C.

The reaction is generally carried out under atmospheric pressure.

The compounds of the formulae (IX) and (X) are generally employed in equimolar amounts; however, it is also possible to use an excess of one compound or the other.

The amide derivatives of the formula (IX) are known (cf. for example EP-A 0 594 179) and/or can be obtained by the methods mentioned therein.

The phenyl derivatives of the formula (X) are generally known compounds of organic chemistry and/or can be obtained in a generally known manner.

The compounds of the formulae (Ia) and (Ib) to be used as starting materials in the process (b) and (c), respectively, according to the invention are compounds according to the invention. The compounds of the formula (Ib) can also be obtained by reducing the carbonyl group in the compounds of the formula (Ia) in a conventional manner.

The alcohols of the formula (III), the thio alcohols of the formula (IV), the compounds of the formula (V), the hydroxylamines of the formula (VI) and the hydrazines of the formula (VII) also to be used as starting materials in the process (b) according to the invention are generally known compounds of organic chemistry and/or can be obtained in a generally known manner.

In the formula (V), A preferably represents a $C_2$- or $C_3$-hydrocarbon chain which is optionally mono- or disubstituted by identical or different substituents, suitable substituents being those mentioned above as substituents for $R^3$ and $R^4$ in the case where $R^3$ and $R^4$ together form a ring.

The halides of the formula (VIII) also to be used as starting materials in the process (c) according to the invention are generally known compounds of organic chemistry.

In the formula (VIII) Hal preferably represents chlorine, bromine or iodine.

In the formula (VIII) $R^{11}$ represents alkyl or optionally substituted benzyl, in each case as defined for $R^4$.

Suitable diluents for the process (a) according to the invention are all inert organic solvents. If appropriate, they can be employed as a mixture with water. Preference is given to using hydrocarbons such as toluene, xylene, tetraline, hexane and cyclohexane, halogenated hydrocarbons such as methylene chloride, chloroform, chlorobenzene and o-dichlorobenzene, alcohols such as methanol, ethanol, glycol, the isomeric propanols, butanols and pentanols, ethers such as diethyl ether, diisopropyl ether, dimethoxyethane, tetrahydrofuran and dioxane, nitriles such as acetonitrile or butyronitrile, amides such as dimethylformamide, sulphoxides such as dimethyl sulphoxide and also sulpholane. Particular preference is given to using alcohols or amides.

Suitable bases for the process (a) according to the invention are all customary acid acceptors.

Preference is given to using tertiary amides such as triethylamine, pyridine, diazabicyclooctane (DABCO), diazabicycloundecene (DBU), diazabicyclononen (DBN), N,N-dimethylaniline, and also alkaline earth metal oxides such as magnesium oxide and calcium oxide, additionally alkali metal carbonates and alkaline earth metal carbonates such as sodium carbonate, potassium carbonate and calcium carbonate, alkali metal hydroxides such as sodium hydroxide and potassium hydroxide, and furthermore alkoxides such as sodium ethoxide or potassium tertbutocid. Particular preference is given to alkali metal hydroxides and alkali metal alkoxides.

If appropriate, the process (a) according to the invention is carried out in the presence of a phase transfer catalyst. Suitable phase transfer catalysts are for example ammonium compounds such as tetraoctylammonium bromide or benzyltriethylammonium chloride.

The reaction temperature of the process (a) according to the invention can be varied within a relatively wide range. Generally, the reaction is carried out at temperatures between −10° C. and 150° C., preferably between 0° C. and 100° C.

The reaction is generally carried out under atmospheric pressure.

In general, an equimolar amount of base is employed. However, it is also possible to carry out the reaction with an excess of base.

Work-up is carried out in a conventional manner.

Suitable diluents for carrying out the process (b) according to the invention are inert organic solvents. These include in particular aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride; ethers such as diethyl ether, diisopropyl ether, dioxane, tetrahydrofuran or ethylene glycol dimethyl ether or ethylene glycol diethyl ether; nitriles such as acetonitrile, propionitrile or benzonitrile; amides such as N,N-dimethylformamide, N,N-dimethylacetamide, N-methylformanilide, N-methyl pyrrolidone or hexamethylphosphoric triamide; alcohols such as methanol, ethanol, n- or i-propanol, ethylene glycol monomethyl ether, ethylene glycol monoethyl ether, diethylene glycol monomethyl ether, diethylene glycol monoethyl ether, if appropriate their mixtures with water or pure water.

If appropriate, the variant (b1) of the process (b) according to the invention is carried out in the presence of a catalyst. These include, for example, acids, for example toluenesulphonic acid, salts of alkali metal hydroxides with acids, salts of amines (in particular of pyridine with inorganic acids, for example pyridine hydrochloride).

If appropriate, the variant (b2) of the process (b) according to the invention is carried out in the presence of a suitable acid or base (as water-eliminating agent). Suitable acids and bases are, for example, p-toluenesulphonic acid, sulphuric acid, pyridine hydrochloride or sodium acetate.

In the practice of the process (b) according to the invention, the reaction temperatures may be varied within a relatively wide range. In general, the process is carried out at temperatures between 0° C. and +150° C., preferably at temperatures between 30° C. and +120° C. (using, if appropriate, a water separator).

The process (b) according to the invention is usually carried out under atmospheric pressure. However, it is also possible to operate under elevated or reduced pressure.

In the practice of the process (b) according to the invention, generally 1.0 to 3.0 mol, preferably 1.0 to 2.0 mol, of the compounds of the formulae (III), (IV), (V), (VI) or (VII) are employed per mole of the compound of the formula (Ia). Known methods are used for carrying out the reaction, for work-up and for isolating the reaction products.

Suitable diluents for carrying out -the process (c) according to the invention are all customary inert organic solvents. Preference is given to using aliphatic, alicyclic or aromatic hydrocarbons such as, for example, petroleum ether, hexane, heptane, cyclohexane, methylcyclohexane, benzene, toluene, xylene or decalin; halogenated hydrocarbons such as, for example, chlorobenzene, dichlorobenzene, dichloromethane, chloroform, carbon tetrachloride, dichloroethane or trichloroethane; ethers such as diethyl ether, diisopropyl ether, methyl-t-butyl ether, methyl-t-amyl ether, dioxane, tetrahydrofuran, 1,2-dimethoxyethane, 1,2-diethoxyethane or anisole; ketones such as acetone, butanone, methyl-isobutyl ketone or cyclohexanone; nitriles such as acetonitrile, propionitrile, n- or i-butyronitrile or benzonitrile; amides such as N,N-dimethylformamide, N,N-dimethylacetamide, N-methylformanilide, N-methylpyrrolidone or hexamethylphosphoric triamide; esters such as methyl acetate or ethyl acetate; sulphoxides, such as dimethyl sulphoxide; sulphones such as sulpholane.

Suitable bases for carrying out the process (c) according to the invention are all customary inorganic and organic bases. Preference is given to using alkali metal hydroxides (such as sodium hydroxide or potassium hydroxide), alkali metal alkoxides (such as sodium methoxide or sodium ethoxide), butyllithium or sodium hydride.

In the practice of the process (c) according to the invention, the reaction temperatures can be varied within a relatively wide range. Generally, the reaction is carried out at temperatures between −20° C. and +180° C., preferably at temperatures between 0° C. and 130° C.

The process (c) according to the invention is generally carried out under atmospheric pressure. However, it is also possible to operate under elevated or reduced pressure.

In the practice of the process (c) according to the invention, generally 1.0 to 5.0 mol, preferably 1.0 to 3.0 mol, of the halide of the formula (VIII) are employed per mole of the compound of the formula (Ib). Customary methods are used for carrying out the reaction and for work-up.

The active compounds are suitable for controlling animal pests, in particular insects, arachnids and nematodes, encountered in agriculture, in forestry, in the protection of stored products and of materials, and in the hygiene sector, and have good plant safety and low toxicity to warmblooded animals. They are preferably used as crop protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Spodoptera litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include Pratylenchus spp., *Radopholus similis, Ditylenchus dipsaci, Tylenchulus semipenetrans,* Heterodera spp., Globodera spp., Meloidogyne spp., Aphelenchoides spp., Longidorus spp., Xiphinema spp. and Trichodorus spp.

The compounds of the formula (I) according to the invention in particular have outstanding insecticidal and acaracidal activity.

They are particularly successfully used for controlling plant-damaging insects, for example against mustard beetle larvae (*Phaedon cochleariae*), the green rice leaf hopper (*Nephotettix cincticeps*), caterpillars of the owlet moth (*Spodoptera frugiperda*), and green peach aphids (*Myzus persicae*) or for controlling plant-damaging mites, for example against the common spider mite (*Tetranychus urticae*).

The active compounds can be converted to the customary formulations, such as solutions, emulsions, wettable powders, suspensions, powders, dusting agents, pastes, soluble powders, granules, suspoemulsion concentrates, natural and synthetic materials impregnated with active compound and very fine capsules in polymeric substances.

These formulations are produced in a known manner, for example by mixing the active compounds with extenders, that is liquid solvents and/or solid carriers, if appropriate with the use of surfactants, that is emulsifiers and/or dispersing agents and/or foam-forming agents.

If the extender used is water, it is possible to use, for example, organic solvents as auxiliary solvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

Suitable solid carriers are:

for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifiers and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; suitable dispersing agents are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%, and preferably in addition extenders and/or surfactants.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Examples of particularly advantageous mixing components are the following:

Fungicides:

2-aminobutane; 2-anilino4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxy-phenyl) acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino [alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezine, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclofos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides:

bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin, *Bacillus thuringiensis,* bendiocarb, benfuracarb, bensultap, beta-cyfluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, CGA 157419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimfos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonofos, formothion, fosthiazate, fubfenprox, furathiocarb, HCH, heptenophos, hexaflumuron, hexythiazox, imidacloprid, iprobenfos, isazofos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemeton M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozine, pyrachlofos, pyridaphenthion, pyresmethrin, pyrethrum, pyridaben, pyrimidifen, pyriproxyfen, quinalphos, RH 5992, salithion, sebufos, silafluofen, sulfotep, sulprofos, tebufenozide, tebufenpyrad, tebupirimifos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimethacarb, vamidothion, XMC, xylylcarb, YI 5301/5302, zetamethrin.

A mixture with other known active compounds, such as herbicides, or with fertilizers and growth-regulators is also possible.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene and stored-product pests, the active compound has an excellent residual action on wood and clay as well as a good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp. and Solenopotes spp.

From the order of the Mallophagida and the sub-orders Amblycerina and Ischnocerina, for example, Trimenopon spp., Menopon spp., Trinoton spp., Bovicola spp., Werneckiella spp., Lepikentron spp., Damalina spp., Trichodectes spp. and Felicola spp.

From the order of the Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopyslla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta amencana, Blattela germanica* and Supella spp.

From the sub-class of the Acaria (Acarida) and the orders of the Meta- and Mesostigmata, for example, Argas spp., Omithodorus spp., Otabius spp., Ixodes spp., Amblyomma spp., Boophilus spp., Dermacentor spp., Haemophysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

For example, they have a good development-inhibitory activity against all larvae of the fly *Lucilia cuprina.*

The active compounds of the formula (I) according to the invention are also suitable for controlling arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, caged birds, aquarium fish, and so-called experimental animals, such as, for example, hamsters, guinea-pigs, rats and mice. By controlling these arthropods, it is intended to reduce deaths and decreased performances (in meat, milk, wool, hides, eggs, honey and the like), so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boluses, the feed-through method, suppositories, by parenteral administration, such as, for example, by means of injections (intramuscular, subcutaneous, intravenous, intraperitoneal and the like), implants, by nasal administration, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of I to 80% by weight, either directly or after dilution by a factor of 100 to 10,000, or they may be used in the form of a chemical bath.

Furthermore, it has been found that the compounds of the formula (I) according to the invention have a potent insecticidal action against insects which destroy industrial materials.

The following insects may be mentioned by way of preferred examples but without any limitation:

Beetles, such as

*Hylotrupes bajulus, Chlorophorus pilosis, Anobium punctatum, Xestobium rufovillosum, Ptilinus pecticomis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec., Tryptodendron spec., *Apate monachus, Bostrychus capucins, Heterobostrychus brunneus,* Sinoxylon spec. and *Dinoderus minutus.*

Dermapterans, such as

*Sirex juvencus, Urocerus gigas, Urocerus gigas taignus* and *Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus.*

Bristletails, such as

*Lepisma saccharina.*

Industrial materials are to be understood as meaning, in the present context, non-live materials, such as, preferably, synthetic materials, glues, sizes, paper and board, leather, wood and timber products, and paint.

The materials to be very particularly preferably protected against attack by insects are wood and timber products.

Wood and timber products which can be protected by the composition according to the invention or mixtures comprising such a composition are to be understood as meaning, for example, construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-like solvents having an evaporation number of above 35 and a flashpoint of above 30° C., preferably above 45° C. Substances which are used as such oily and oil-like solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-like solvents of low volatility and having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ether, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The artificial resin used as the binder can be employed in the form of an emulsion, dispersion or solution. Up to 10% by weight of bitumen or bituminous substances can also be used as binder. In addition, colorants, pigments, water repellents, odour-masking substances and inhibitors or anticorrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluenesulphonic esters.

Fixatives are chemically based on polyvinyl alkyl ethers, such as, for example, polyvinyl methyl ether, or ketones, such as benzophenone or ethylenebenzophenone.

Particularly suitable as a solvent or diluent is also water, if appropriate as a mixture with one or more of the above-mentioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly incorporated into the present application by reference.

Very particularly preferred components which may be admixed are insecticides, such as chlorpyrifos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The preparation and the use of the active compounds according to the invention can be seen from the examples which follow.

PREPARATION EXAMPLES

Example 1

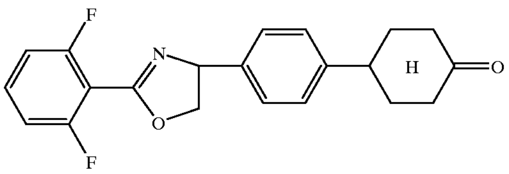

(Process a)

At 5° C., 3.5 ml (0.05841 mol) of 45% strength aqueous sodium hydroxide solution are added dropwise to 20.8 g (0.0531 mol) of 2-(2,6-difluorobenzoylamido)-2-[4-(4-oxo-cyclohexyl)-phenyl]-1-chloroethane in 130 ml of absolute dimethylformamide. The reaction mixture is allowed to warm to room temperature and stirred overnight. The solvent is subsequently distilled off using water pump vacuum and the residue is taken up in 300 ml of ethyl acetate, washed repeatedly with water, dried over sodium sulphate, filtered, concentrated and purified by column chromatography (silica gel, toluene/ethyl acetate 911).

16.5 g (79.6% of theory) of 2-(2,6-difluorophenyl)-4-[4-(4-oxo-cyclohexyl)-phenyl]-1,3-oxazoline of a logp*)=2.28 are obtained.

*) logp: Logarithm to base ten of the n-octanol/water partition coefficient, determined by reversed phase HPLC analysis using $H_2O/CH_3CN$.

Preparation of the starting material (II-1)

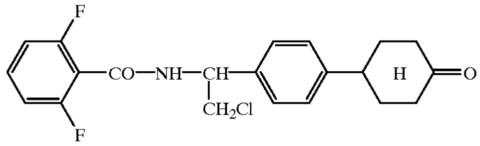

At 5° C., 17.4 g (0.1 mol) of 4-phenylcyclohexanone and 24.3 g (0.1 mol) of N-(2-chloro-1-methoxyethyl)-2,6-difluorobenzamide in 100 ml of absolute methylene chloride are admixed with 48.7 g (0.3 mol) of anhydrous iron(III) chloride. Over a period of 4 hours, the reaction mixture is allowed to warm to room temperature and is then stirred at this temperature for 16 hours.

The reaction mixture is subsequently stirred into 1 liter of ice water and the organic phase is separated off, dried over sodium sulphate, filtered, concentrated using water pump vacuum and purified by column chromatography (silica gel, methylene chloride/ethyl acetate).

10.4 g (26.6% of theory) of 2-(2,6-difluorobenzoylamido)-2-[4-(4-oxo-cyclohexyl)phenyl]-chloroethane of logp*)=2.54 are obtained.

*) logp: Logarithm to base ten of the n-octanol/water partition coefficient, determined by reversed phase HPLC analysis using $H_2O/CH_3CN$.

Example 2

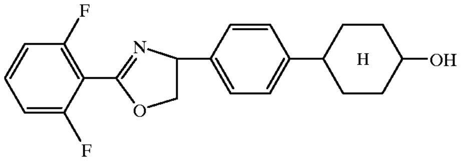

(Process a)

At 5° C., 0.8 ml (0.01296 mol) of 45% strength aqueous sodium hydroxide solution are added dropwise to 5 g (0.01296 mol) of 2-(2,6-difluorobenzoylamido)-2-[4-(4-hydroxycyclohexyl)-phenyl]-1-chloroethane in 50 ml of dimethylformamide. The reaction mixture is allowed to warm to room temperature, stirred overnight and then poured into 150 ml of ice water. The mixture is then extracted with dichloromethane, dried over sodium sulphate, filtered, concentrated and purified by column chromatography (silica gel, toluene/ethyl acetate 1/1).

3.4 g (73.5% of theory) of 2-(2,6-difluorophenyl)-4-[4-(4-hydroxycyclohexyl)phenyl]-1,3-oxazoline are obtained as a pure diastereomer of logp*)=2.53.

*) logp: Logarithm to base ten of the n-octanol/water partition coefficient, determined by reversed phase HPLC analysis using $H_2O/CH_3CN$.

Example 3

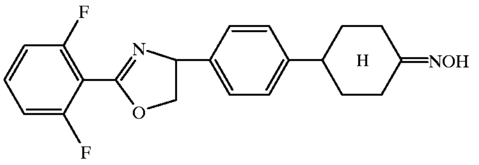

(Process b, variant b2)

A solution of 21 g (0.0247 mol) of sodium acetate in 10 ml of water and then 1.7 g (0.0247 mol) of hydroxylamine hydrochloride are added to 8.8 g (0.0247 mol) of 2-(2,6-difluorophenyl)-4-[4-(4-oxo-cyclohexyl)-phenyl]-1,3-oxazoline (Example 1) in 100 ml of 1,2-dimethoxyethane. The reaction mixture is stirred at room temperature for 16 hours.

The solvent is distilled off and the residue is taken up in 300 ml of ethyl acetate, washed with 200 ml of water, dried over sodium sulphate, filtered, concentrated and purified by column chromatography (silica gel, toluene/ethyl acetate 9/1).

6.7 g (60.9% of theory) of 2-(2,6-difluorophenyl)-4-[4-(4-oximino-cyclohexyl)phenyl]-1,3-oxazoline of logp*)=2.57 are obtained.

*) logp: Logarithm to base ten of the n-octanol/water partition coefficient, determined by reversed phase HPLC analysis using $H_2O/CH_3CN$.

Example 4

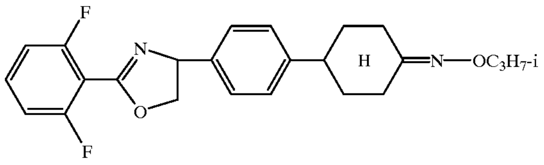

(Process b, variant b2)

0.67 g (0.0048 mol) of potassium carbonate and 0.48 ml (0.0048 mol) of isopropyl iodide are added to 0.9 g (0.0024 mol) of $^{2}$-($^{2}$,$^{6}$-difluorophenyl)-4-[4-(4-oximinocyclohexyl)-phenyl]-1,3-oxazoline (Example 3) in 15 ml of absolute acetonitrile.

After the addition of two drops of tetraethoxyethylene-ammonium hydroxide, the reaction mixture is stirred under reflux overnight, and three drops of tetrabutylammonium hydroxide are then added and the mixture is once more stirred under reflux overnight. The solvent is distilled off and the reaction mixture is poured into 100 ml of ethyl acetate, washed with 100 ml of water, dried over sodium sulphate, filtered, concentrated and purified by column chromatography (silica gel, toluene/ethyl acetate 8/2).

0.2 g (20.2% of theory) of 2-(2,6-difluorophenyl)4-[4-(4-1-propoximino-cyclohexyl)-phenyl]-1,3-oxazoline of logp*)=4.50 are obtained.

*) logp: Logarithm to base ten of the n-octanol/water partition coefficient, determined by reversed phase HPLC analysis using $H_2O/CH_3$ CN.

Example 5

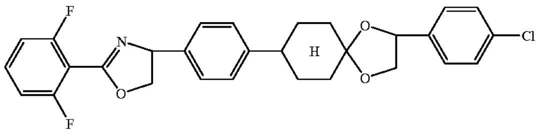

(Process b, variant b1)

0.9 g (0.005 mol) of (4-chlorophenyl)-ethane-1,2-diol and 20 ml of toluene are added to 1.8 g (0.005 mol) of 2-(2,6-difluorophenyl)-4-[4-(4-oxo-cyclohexyl)phenyl]-1,3-oxazoline (Example 1) in 10 ml of n-butanol. After the addition of 1 drop of glacial acetic acid, the reaction mixture is stirred under reflux for 3 hours. A spatula tip of p-toluenesulphonic acid is added, and stirring is continued for a further hour. The solvent is distilled off and the residue is purified by column chromatography (silica gel, toluene/ethyl acetate 10/0.5).

1.5 g (58.9% of theory) of 2-(2,6-difluorophenyl)-4-[4-(4-p-chlorophenylethylenedioxo-cyclohexyl)-phenyl]-1,3-oxazoline of logp*)=5.37 are obtained.

*) logp: Logarithm to base ten of the n-octanol/water partition coefficient, determined by reversed phase HPLC analysis using $H_2O/CH_3CN$.

Using the methods of Examples 1 to 5 and/or the general preparation procedures, the compounds of the formula (I) listed in Table 1 below were obtained:

(I)

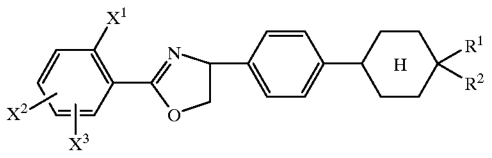

TABLE 1

| Ex. No. | $X^1$ | $X^2$ | $X^3$ | $R^1$ | $R^2$ | mp (° C.) or logp*) |
|---|---|---|---|---|---|---|
| 6 | F | 6-F | H | $=NOC_2H_5$ | | 4.00 |
| 7 | F | 6-F | H | H | OH | 2.74 |
| 8 | F | 6-F | H | $OCH_3$ | $OCH_3$ | 3.80 |
| 9 | F | 6-F | H | 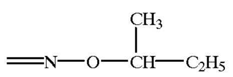 | | 4.96 |

TABLE 1-continued
| Ex. No. | $X^1$ | $X^2$ | $X^3$ | $R^1$ | $R^2$ | mp (° C.) or logp*) |
|---|---|---|---|---|---|---|
| 10 | F | 6-F | H | 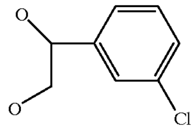 | | 5.22 |
| 11 | F | 6-F | H | 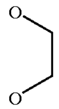 | | 3.46 |
| 12 | F | 6-F | H | 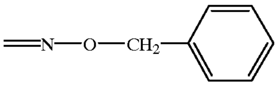 | | 4.70 |
| 13 | F | 6-F | H | 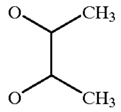 | | 4.23 (A isomer)[1)]<br>4.31 (B isomer) |
| 14 | F | 6-F | H | 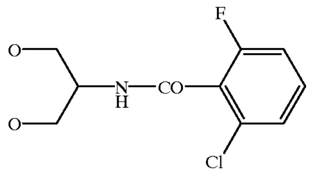 | | 90–100° C. |
| 15 | F | 6-F | H | 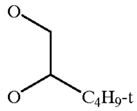 | | 5.41 (A isomer)[1)]<br>5.48 (B isomer) |
| 16 | F | 6-F | H | 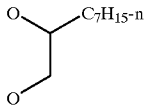 | | 6.25 (A isomer)[1)]<br>6.31 (B isomer) |
| 17 | F | 6-F | H | 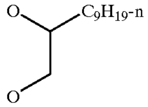 | | 7.12 (A isomer)[1)]<br>7.20 (B isomer) |
| 18 | F | 6-F | H | 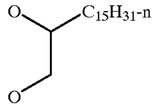 | | 9.0 |
| 19 | F | 6-F | H | $OC_4H_9$ | $OC_4H_9$ | 6.77 (A isomer)[1)]<br>6.86 (B isomer) |
| 20 | F | 6-F | H | 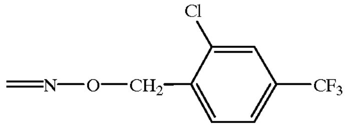 | | 5.91 |
| 21 | F | 6-F | H | 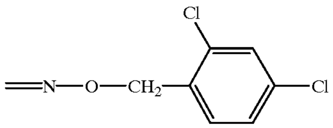 | | 5.92 |

TABLE 1-continued
| Ex. No. | $X^1$ | $X^2$ | $X^3$ | $R^1$ | $R^2$ | mp (° C.) or logp[*)] |
|---|---|---|---|---|---|---|
| 22 | F | 6-F | H | 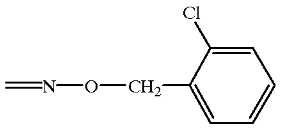 | | 5.21 |
| 23 | F | 6-F | H | 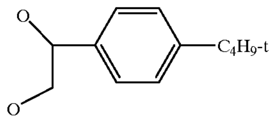 | | 6.16 |
| 24 | F | 6-F | H | 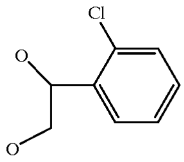 | | 5.60 |
| 25 | F | 6-F | H | 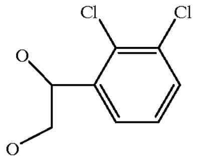 | | 6.07 |
| 26 | F | 6-F | H | 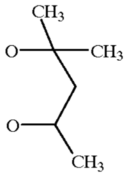 | | 5.12 (A isomer)[1)]<br>5.19 (B isomer) |
| 27 | F | 6-F | H | 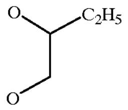 | | 4.43 |
| 28 | F | 6-F | H | 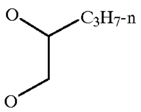 | | 4.52 |
| 29 | F | 6-F | H | 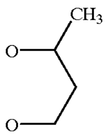 | | 3.95 (A isomer)[1)]<br>3.98 (B isomer) |
| 30 | F | 6-F | H | 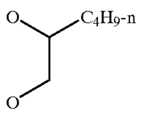 | | 5.35 (A isomer)[1)]<br>5.40 (B isomer) |

TABLE 1-continued
| Ex. No. | $X^1$ | $X^2$ | $X^3$ | $R^1$ | $R^2$ | mp (° C.) or logp*) |
|---|---|---|---|---|---|---|
| 31 | F | 6-F | H | 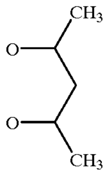 | | 4.52 (A isomer)1)<br>4.84 (B isomer) |
| 32 | F | 6-F | H | 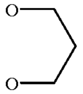 | | 3.47 |
| 33 | F | 6-F | H | 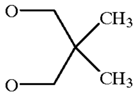 | | 4.50 |
| 34 | F | 6-F | H | 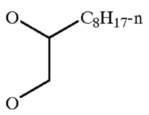 | | 7.19 (A isomer)1)<br>7.28 (B isomer) |
| 35 | F | 6-F | H | 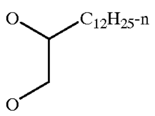 | | >12 |
| 36 | F | 6-F | H | $=NOC_4H_9$-n | | 4.95 |
| 37 | F | 6-F | H | 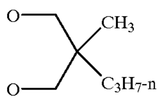 | | 5.46 |
| 38 | F | 6-F | H | 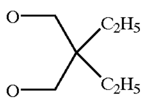 | | 5.40 |
| 39 | F | 6-F | H | 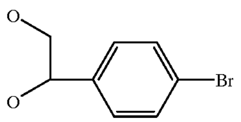 | | 5.36 (A isomer)1)<br>5.51 (B isomer) |
| 40 | F | 6-F | H | 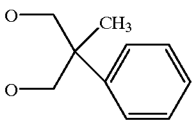 | | 5.11 |
| 41 | F | 6-F | H | 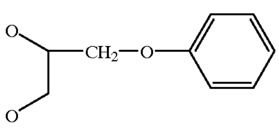 | | 4.73 (A isomer)1)<br>4.75 (B isomer) |
| 42 | F | 6-F | H | 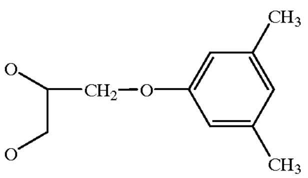 | | 5.44 (A isomer)1)<br>5.48 (B isomer) |

TABLE 1-continued
| Ex. No. | $X^1$ | $X^2$ | $X^3$ | $R^1$ | $R^2$ | mp (° C.) or logp[*)] |
|---|---|---|---|---|---|---|
| 43 | F | 6-F | H | 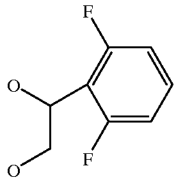 | | 4.77 (A isomer)[1)]<br>4.86 (B isomer) |
| 44 | F | 6-F | H | 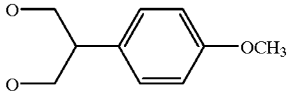 | | 4.61 |
| 45 | F | 6-F | H | 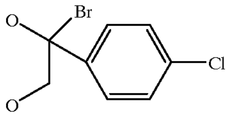 | | 5.96 (A isomer)[1)]<br>6.20 (B isomer) |
| 46 | F | 6-F | H | 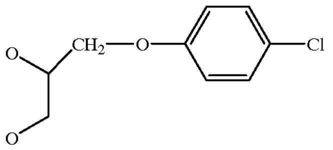 | | 5.10 (A isomer)[1)]<br>5.16 (B isomer) |
| 47 | F | 6-F | H | 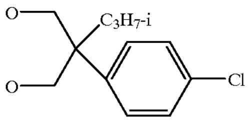 | | 6.15 |
| 48 | F | 6-F | H | 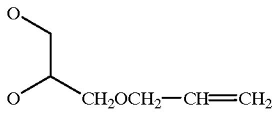 | | 4.21 |
| 49 | F | 6-F | H | 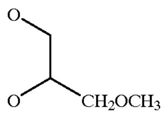 | | 3.57 (A isomer)[1)]<br>3.60 (B isomer) |
| 50 | F | 6-F | H | 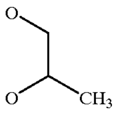 | | 3.89 |
| 51 | F | 6-F | H | 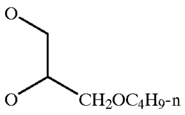 | | 4.97 (A isomer)[1)]<br>5.00 (B isomer) |
| 52 | F | 6-F | H | 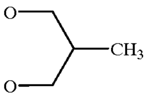 | | 3.99 |
| 53 | F | 6-F | H | 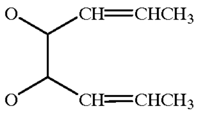 | | 5.23 (A isomer)[1)]<br>5.37 (B isomer) |

TABLE 1-continued
| Ex. No. | $X^1$ | $X^2$ | $X^3$ | $R^1$ | $R^2$ | mp (° C.) or logp*) |
|---|---|---|---|---|---|---|
| 54 | F | 6-F | H | 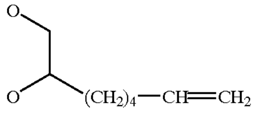 | | 5.65 (A isomer)[1)]<br>5.70 (B isomer) |
| 55 | F | 6-F | H | $=NOCH_2CH=CH_2$ | | 4.16 |
| 56 | F | 6-F | H | $=NOCH_3$ | | 3.60 |
| 57 | F | 6-Cl | H | $=O$ | | 3.09 |
| 58 | F | 6-F | H | 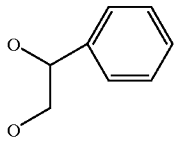 | | 4.78 (A isomer)[1)]<br>4.87 (B isomer) |
| 59 | F | 6-F | H | 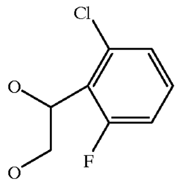 | | 5.14 |
| 60 | F | 6-F | H | 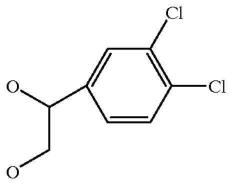 | | 5.65 |
| 61 | F | 6-F | H | 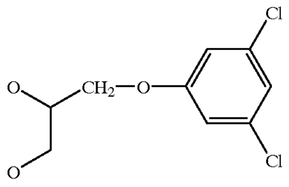 | | |
| 62 | F | 6-F | H | 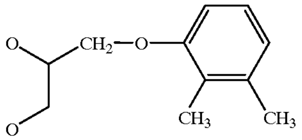 | | |
| 63 | F | 6-F | H | 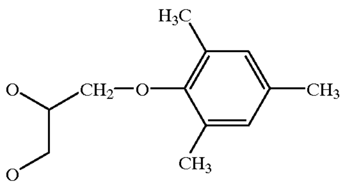 | | |
| 64 | F | 6-F | H | 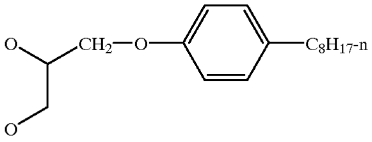 | | |

TABLE 1-continued
| Ex. No. | $X^1$ | $X^2$ | $X^3$ | $R^1$ | $R^2$ | mp (° C.) or logp*) |
|---|---|---|---|---|---|---|
| 65 | F | 6-F | H | 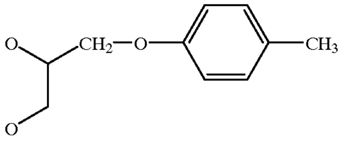 | | |
| 66 | F | 6-F | H | 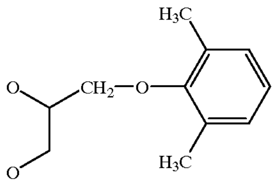 | | |
| 67 | F | 6-F | H | 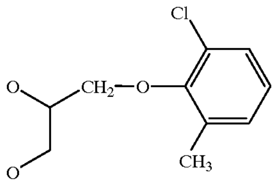 | | |
| 68 | F | 6-F | H | 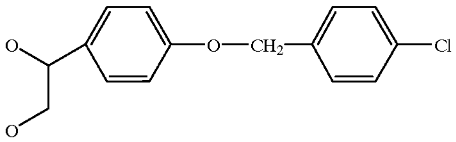 | | |
| 69 | F | 6-F | H | 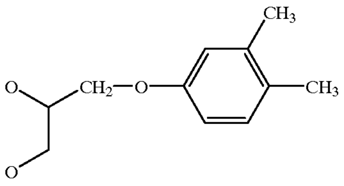 | | |
| 70 | F | 6-F | H | 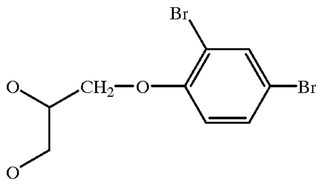 | | |
| 71 | F | 6-F | H | 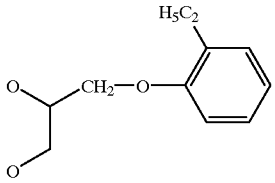 | | |
| 72 | F | 6-F | H | 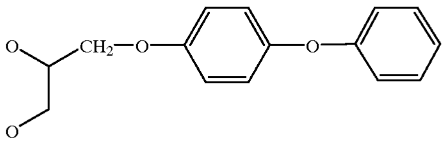 | | |

TABLE 1-continued
| Ex. No. | $X^1$ | $X^2$ | $X^3$ | $R^1$ | $R^2$ | mp (° C.) or logp*) |
|---|---|---|---|---|---|---|
| 73 | F | 6-F | H | 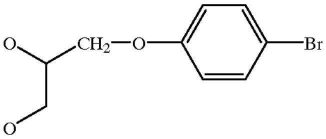 | | |
| 74 | F | 6-F | H | 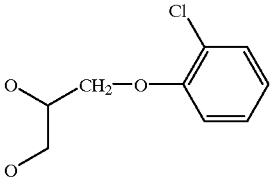 | | |
| 75 | F | 6-F | H | 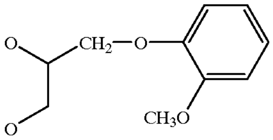 | | |
| 76 | F | 6-F | H | 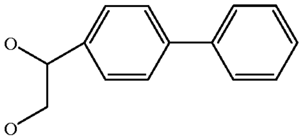 | | |
| 77 | F | 6-F | H | 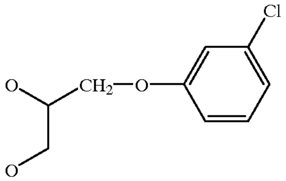 | | |
| 78 | F | 6-F | H | 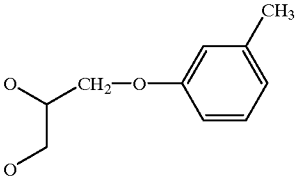 | | |
| 79 | F | 6-F | H | 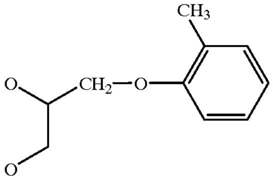 | | |
| 80 | F | 6-F | H | 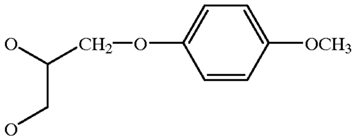 | | |
| 81 | F | 6-F | H | 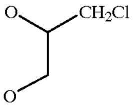 | | |

TABLE 1-continued

| Ex. No. | $X^1$ | $X^2$ | $X^3$ | $R^1$ | $R^2$ | mp (° C.) or logp*) |
|---|---|---|---|---|---|---|
| 82 | F | 6-F | H | 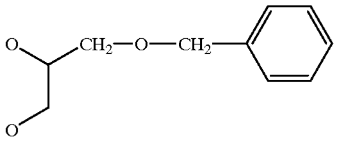 | | |
| 83 | F | 6-F | H | $-OC^3H_7$-n | $-OC_3H_7$-n | |
| 84 | F | 6-F | H | $-OC_6H_{13}$-n | $-OC_{61}H_{13}$-n | |

*)logp: Logarithm to base ten of the n-octanol/water partition coefficient, determined by reversed phase HPLC analysis using $H_2O/CH_3CN$.
1)A and B isomer: possible geometric isomers

USE EXAMPLES

In the use examples below, the compounds listed below are used as comparative substances:

(A)

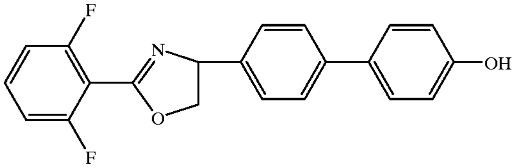

(B)

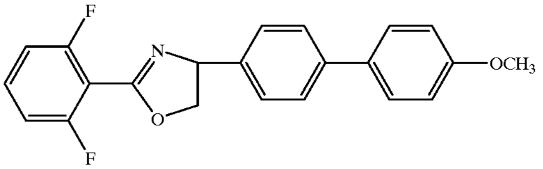

(C)

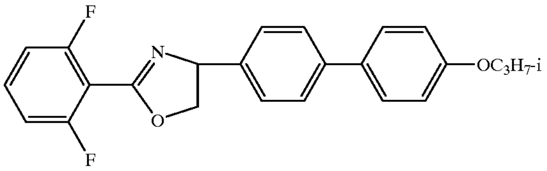

(D)

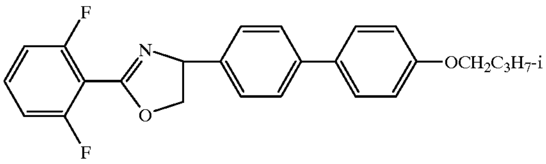

(E)

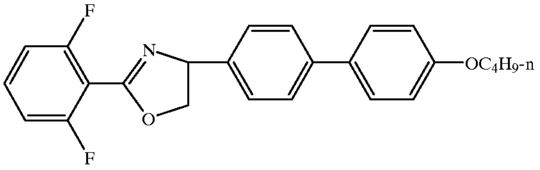

-continued (F)

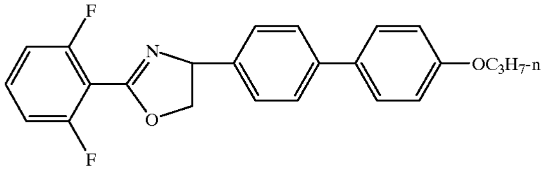

(all compounds known from EP-A 0 696 584)

Example A

Phaedon larvae test

Solvent: 7 parts by weight of dimethylformamide

Emulsifier: 1 part by weight of alkylaryl polyglycol ether

To produce a suitable preparation of active compound, I part by weight of active compound is mixed with the stated amount of solvent and the stated amount of emulsifier, and the concentrate is diluted with water to the desired concentration.

Cabbage leaves (*Brassica oleracea*) are treated by being dipped into the active compound preparation of the desired concentration and are infested with mustard beetle larvae (*Phaedon cochleariae*), while the leaves are still moist.

After the desired period of time, the destruction in % is determined. 100% means that all the beetle larvae have been killed; 0% means that none of the beetle larvae have been killed.

In this test, at an exemplary active compound concentration of 0.01%, for example the compounds of Preparation Examples 4 and 8 cause a destruction of 90% and the compounds of the Preparation Examples 5, 6, 9, 10, 13, 15, 17 and 20 cause a destruction of 100%, in each case after 7 days, whereas the known compounds (A) and (B) showed no activity.

Example B

*Spodoptera frugiperda* test

Solvent: 7 parts by weight of dimethylformamide

Emulsifier: 1 part by weight of alkylaryl polyglycol ether

To produce a suitable preparation of active compound, I part by weight of active compound is mixed with the stated amount of solvent and the stated amount of emulsifier, and the concentrate is diluted with water to the desired concentration.

Cabbage leaves (*Brassica oleracea*) are treated by being dipped into the active compound preparation of the desired concentration and are infested with caterpillars of the owlet moth (*Spodoptera frugiperda*), while the leaves are still moist.

After the desired period of time, the destruction in % is determined. 100% means that all the caterpillars have been killed; 0% means that none of the caterpillars have been killed.

In this test, at an exemplary active compound concentration of 0.1%, for example the compounds of Preparation Examples 4, 5, 6, 9, 10, 17 and 19 caused a destruction of 100%, in each case after 7 days, whereas the known compound (B) showed no activity.

Example C

Nephotettix test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the active compound preparation of the desired concentration and are infested with the green rice leaf hopper (*Nephotettix cincticeps*), while the seedlings are still moist.

After the desired period of time, the destruction in % is determined. 100% means that all the leaf hoppers have been killed; 0% means that none of the leaf hoppers have been killed.

In this test, at an exemplary active compound concentration of 0.1%, for example the compounds of the following Preparation Examples caused the following destruction:

1=90%; 6=100% and 13=80%;

in each case after 6 days, whereas the known compounds (B), (C), (D) and (E) showed no activity.

Example D

Myzus test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Seedlings of the broad bean (*Vicia faba*) which are infested with peach aphids (*Myzus persicae*) are dipped into the active compound preparation of the desired concentration and placed into a plastic box.

After the desired period of time, the destruction in % is determined. 100% means that all the aphids have been killed; 0% means that none of the aphids have been killed.

In this test, at an exemplary active compound concentration of 0.1%, for example the compounds of the following preparation examples caused the following destruction:

4=100%; 15, 16, 17=90% and 21=80%;

in each case after 6 days, whereas the known compound (A) showed no activity.

Example E

Tetranychus test (OP resistant/dip treatment)

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with emulsifier-containing water to the desired concentrations.

Bean plants (*Phaseolus vulgaris*) which are heavily infested by all stages of the common spider mite (*Tetranychus urticae*) are dipped into the active compound preparation of the desired concentration.

After the desired period of time, the activity in % is determined. 100% means that all the spider mites have been killed; 0% means that none of the spider mites have been killed.

In this test, at an exemplary active compound concentration of 0.0001%, for example the compounds of Preparation Examples 4, 5, 6, 9, 10, 12, 13, 15, 16, 17, 19, 20, 21, 22, 23, 24 and 25 caused a destruction of 98%, in each case after 13 days, whereas the known compounds (A) and (F) effected no destruction and a destruction of only 45%, respectively.

Example F

Fly larvae test/development-inhibitory action

Test animals: All larval stages of *Lucilia cuprina* (OP resistant) [Pupae and adults (without contact with the active compound)]

Solvent: 35 parts by weight of ethylene glycol monomethyl ether 35 parts by weight of nonylphenol polyglycol ether To prepare a suitable formulation, 3 parts by weight of active compound are mixed with 7 parts of the abovementioned solvent-emulsifier mixture, and the resulting emulsion concentrate is diluted with water to the concentration desired in each case.

For each concentration, 30 to 50 larvae are transferred to horse meat (1 $cm^3$) located in glass tubes, and 500 $\mu$l of the test dilution are pipetted onto the meat. The glass tubes are placed into plastic beakers whose bottom is covered with sea sand and kept in a controlled-environment cabinet (26° C.±1.5° C., 70% relative humidity±10%). Larvicidal activity is checked after 24 hours and 48 hours. After the larvae have left (about 72 hours), the glass tubes are removed and perforated plastic lids are placed on the beakers. After 1½ times the development period (hatching of the control flies), the hatched flies and the pupae/puparia are counted.

The criterion for the activity is the death of the treated larvae after 48 hours (larvicidal effect), or inhibition of adults hatching from the pupae or inhibition of pupation. The criterion for the in-vitro activity of a substance is the inhibition of fly development or a standstill of development prior to the adult stage. 100% larvicidal activity means that all the larvae have died after 48 hours. 100% development-inhibitory activity means that no adult flies have hatched.

In this test, for example the compounds of Preparation Examples 5 and 6 exhibited an activity of 100% at an exemplary active compound concentration of 1000 ppm.

We claim:

1. A compound of the formula (I)

(I)

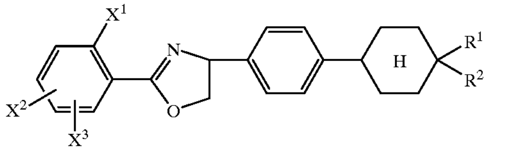

wherein $X^1$ represents halogen, alkyl, alkoxy, alkylthio, halogenoalkyl, halogenoalkoxy, amino, alkylamino or dialkylamino, $X^2$ and $X^3$ are identical or different and each represents hydrogen halogen, alkyl, alkoxy, alkylthio, halogenoalkyl, halogenoalkoxy, amino, alkylamino or dialkylamino, $R^1$ represents hydrogen, —$OR^3$ or —$SR^5$ and $R^2$ represents —$OR^4$, wherein $R^3$ and $R^4$ are identical or different and each represents hydrogen, alkyl, alkenyl or unsubstituted or substituted benzyl, or $R^3$ and $R^4$ join with the hetero atoms to which they are attached and the carbon atom linking these to form an unsubstituted or substituted 5- or 6-membered ring, or $R^1$ and $R^2$ together represent oxygen or represent =N—$OR^5$ or =N—$NR^6R^7$, wherein $R^5$ represents hydrogen, alkyl, alkenyl, alkynyl, halogenoalkyl or unsubstituted or substituted benzyl, $R^6$ represents hydrogen, alkyl, alkenyl, alkynyl, halogenoalkyl or unsubstituted or substituted benzyl, and $R^7$ represents alkyl, alkylcarbonyl, alkoxycarbonyl, unsubstituted or substituted phenyl, phenylcarbonyl or benzyl, or represents —$CONR^5R^6$ or —$SO_2NR^8R^9$ wherein $R^8$ represents hydrogen, alkyl, alkenyl, alkynyl, halogeno-alkyl or unsubstituted or substituted benzyl, and $R^9$ represents alkyl, alkylcarbonyl, alkoxycarbonyl or unsubstituted or substituted phenyl, phenylcarbonyl or benzyl.

2. A compound of the formula (I) according to claim 1 wherein $X^1$ represents fluorine, chlorine, bromine, $C_1$–$C_4$-alkyl, $C_1$–$C_4$alkoxy, $C_1$–$C_4$-alkylthio, $C_1$–$C_4$-halogenoalkyl, $C_1$–$C_4$-halogenoalkoxy, amino, $C_1$–$C_4$-alkylamino or di($C_1$–$C_4$-alkyl)amino, $X^2$ and $X^3$ are identical or different and each represents hydrogen, fluorine, chlorine, bromine, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, amino, $C_1$-$C_4$-alkylamino or di($C_1$–$C_4$-alkyl)amino, $R^1$ represents hydrogen, —$OR^3$ or —$SR^3$ and $R^2$ represents the radical —$OR^4$, or $R^1$ and $R^2$ together represent oxygen, or represent =N—$OR^5$ or =N—$NR^6R^7$, $R^3$ and $R^4$ are identical or different and each represents hydrogen, $C_1$–$C_4$-alkyl or benzyl which is unsubstituted or mono- to trisubstituted, in the phenyl moiety, by identical or different substituents from the group consisting of halogen, $C_1$–$C_4$-alkyl, $C_1$–$C_4$-alkoxy, $C_1$-$C_4$-alkylthio, $C_1$–$C_4$-halogenoalkyl, $C_1$–$C_4$-halogenoalkoxy, $C_1$–$C_4$-halogenoalkylthio, cyano, nitro, di($C_1$–$C_4$-alkyl)amino and $C_1$–$C_4$-alkoxy-carbonyl, or $R^3$ and $R^4$ join with the hetero atoms to which they are attached and the carbon atom linking these to form a 5- or 6-membered ring which is unsubstituted or mono- or disubstituted by identical or different substituents from the group consisting of $C_1$–$C_{18}$alkyl which is unsubstituted or substituted by halogen, $C_1$–$C_6$-alkoxy, $C_2$–$C_6$-alkenyloxy, benzyloxy or phenoxy each of which is unsubstituted or mono- to trisubstituted, mono- or disubstituted, in the ring, by identical or different substituents from the group consisting of halogen, $C_1$–$C_8$-alkyl, $C_1$–$C_4$-alkoxy and phenoxy, and $C_2$–$C_8$-alkenyl phenyl which is unsubstituted or mono- to trisubstituted by identical or different substituents from the group consisting of halogen, $C_1$–$C_4$-alkyl, $C_1$–$C_{14}$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, cyano, nitro, di($C_1$–$C_4$-alkyl)amino, $C_1$–$C_4$-alkoxy-carbonyl, phenyl, which is optionally mono- or disubstituted by identical or different substituents from the group consisting of halogen and $C_1$–$C_4$-alkyl, and benzyloxy which is unsubstituted or mono- or disubstituted in the ring by identical or different substituent from the group consisting of halogen and $C_1$–$C_4$-alkyl and $NR^{12}R^{13}$, $R^{12}$ represents hydrogen, $C_1$–$C_4$-alkyl, $C_2$–$C_4$-alkenyl, $C_2$–$C_4$-alkynyl, $C_1$–$C_4$-halogenoalkyl or benzyl which is unsubstituted or mono- to trisubstituted, in the phenyl moiety, by identical or different substituents from the group consisting of halogen, $C_1$–$C_4$-alkyl, $C_1$–$C_4$-alkoxy, $C_1$–$C_4$-alkylthio, $C_1$-$C_4$-halogenoalkyl, $C_1$–$C_4$-halogenoalkoxy, $C_1$–$C_4$-halogenoalkylthio, cyano, nitro, di($C_1$–$C_4$-alkyl) amino and $C_1$–$C_4$-alkoxycarbonyl, $R^{13}$ represents $C_1$–$C_4$-alkyl, $C_1$–$C_4$-alkyl-carbonyl, $C_1$–$C_4$-alkoxylcarbonyl, or represents phenyl, phenylcarbonyl or benzyl, each of which is unsubstituted or mono- to trisubstituted, in the phenyl moiety, by identical or different substituents from the group consisting of halogen, $C_1$–$C_4$-alkyl, $C_1$–$C_4$-alkoxy, $C_1$–$C_4$-alkylthio, $C_1$-$C_4$-halogenoalkyl, $C_1$–$C_4$-halogenoalkoxy, $C_1$–$C_4$ halogenoalkylthio, cyano, nitro, di($C_1$–$C_4$-alkyl)amino and $C_1$–$C_4$-alkoxy-carbonyl, or represents —$CONR^{14}R^{15}$ or —$SO_2NR^{14}R^{15}$, $R^{14}$ represents hydrogen, $C_1$–$C_4$-alkyl, $C_2$–$C_4$-alkenyl, $C_2$–$C_4$-alkynyl, $C_1$–$C_4$-halogenoalkyl or benzyl which is unsubstituted or mono- to trisubstituted, in the phenyl moiety, by identical or different substituents from the group consisting of halogen, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, cyano, nitro, di($C_1$–$C_4$-alkyl) amino and $C_1$–$C_4$-alkoxy-carbonyl, $R^{15}$ represents $C_1$–$C_4$-alkyl, $C_1$–$C_4$-alkyl-carbonyl, $C_1$–$C_4$-alkoxy-carbonyl, or represents phenyl, phenylcarbonyl or benzyl, each of which is unsubstituted or mono- to trisubstituted, in the phenyl moiety, by identical or different substituents from tho group consisting of halogen, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenalkoxy, $C_1$–$C_4$-halogenoalkylthio, cyano, nitro, di($C_1$–$C_4$-alkyl)amino and $C_1$–$C_4$-alkoxy-carbonyl, $R^5$ represents hydrogen, $C_1$–$C_6$-alkyl, $C_2$–$C_6$-alkenyl, $C_2$–$C_6$-alkynyl, $C_1$–$C_4$-halogenoalkyl or benzyl which is unsubstituted or mono- to trisubstituted, in the phenyl moiety, by identical or different substituents from the group consisting of halogen, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$--$C_4$-halogenoalkylthio, cyano, nitro, di($C_1$–$C_4$-alkyl)amino and $C_1$–$C_4$-alkoxycarbonyl, $R^6$ represents hydrogen, $C_1$–$C_4$-alkyl, $C_2$–$C_4$-alkenyl, $C_2$–$C_4$-alkynyl, $C_1$–$C_4$-halogenoalkyl or benzyl which is unsubstituted or mono- to trisubstituted, in the phenyl moiety, by identical or different substituents from the group consisting of halogen, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, cyano, nitro, di($C_1$–$C_4$-alkylamino and $C_1$–$C_4$-alkoxy carbonyl, $R^7$ represents $C_1$–$C_4$alkyl, $C_1$–$C_4$-alkyl-carbonyl, $C_1$–$C_4$-alkoxy-carbonyl, or represents phenyl, phenylcarbonyl or benzyl, each of which is unsubstituted or mono- to trisubstituted, in the phenyl moiety, by identical or different substituents from the group consisting of halogen, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, cyano, nitro, di($C_1$–$C_4$-alkyl)amino and $C_1$–$C_4$-alkoxy-carbonyl, or represents —$CONR^8R^9$ or —$SO_2NR^8R^9$, $R^8$ represents hydrogen, $C_1$–$C_4$-alkyl, $C_1$–$C_4$-alkenyl, $C_1$–$C_4$-alkynyl, $C_1$–$C_4$-halogenoalkyl or benzyl which is unsubstituted or mono- to trisubstituted, in the phenyl moiety, by identical or different substituents from the group consisting of halogen, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, cyano, nitro, di($C_1$–$C_4$-alkyl) amino and $C_1$–$C_4$-alkoxy-carbonyl, and $R^9$ represents $C_1$–$C_4$-alkyl, $C_1$–$C_4$-alkyl-carbonyl, $C_1$–$C_4$-alkoxy-carbonyl, or represents phenyl, phenylcarbonyl or benzyl, each of which is unsubstituted or mono- to unsubstituted, in the phenyl moiety, by identical or different substituents from the group consisting of halogen, $C_1$–$C_4$-alkyl, $C_1$–$C_4$-alkoxy, $C_1$–$C_4$-alkylthio, $C_1$–$C_4$-halogenalkyl, $C_1$–$C_4$-halogenoalkoxy, $C_1$–$C_4$-halogenoalkylthio, cyano, nitro, di($C_1$–$C_4$-alkyl)amino and $C_1$–$C_4$-alkoxy-carbonyl.

3. A compound of tho formula (I) according to claim 1 wherein $X^1$ represents fluorine, chlorine or methyl, $X^2$ and $X^3$ are identical or different and each represents hydrogen, or represents fluorine, chlorine, methyl, ethyl, methoxy, methylthio, tri-fluoromethyl, trifluoromethoxy, amino, dimethylamino or diethylamino, $R^1$ represents hydrogen, —$OR^3$ or —$SR^3$ and $R^2$ represents the radical —$OR^4$ or $R^1$ and $R^2$ together represent oxygen, or represent =N—$OR^6$ or =N $NR^6R^7$, $R^3$ and $R^4$ are identical or different and each represents hydrogen, methyl, ethyl, n- or i-propyl, n,, i-, s- or t-butyl; or represents benzyl which is unsubstitutod or mono- or disubstituted, in the phenyl moiety, by identical or different substituents from the group consisting of fluorine chlorine, bromine, methyl, ethyl, n- or i-propyl, n-, i-, s- or t-butyl; methoxy, ethoxy, methylthio, trifluoromethyl, trifluoromethoxy, trifluoromethylthio, cyano, nitro, dimethylamino, diethylamino, methoxycarbonyl and ethoxycarbonyl, or $R^3$ and $R^4$ join with the hetero atoms to which they are attached and the carbon atom linking these to form a 5- or 6-membered ring which is unsubstituted or mono- to trisubstituted, mono- or disubstituted, by identical or different substituents, suitable substituents being $C_1$–$C_{18}$-alkyl which is unsubstituted or substituted by fluorine, chlorine, methoxy, ethoxy, n- or i-propoxy, n-butyloxy, allyloxy, benzyloxyl which is in each case unsubstituted or mono-to trisubstituted, mono- or disubstituted, in the ring, by identical or different substituents from the group consisting of fluorine, chlorine, bromine, methyl, ethyl, methoxy, ethoxy and phenoxy, and phenoxy, $C_2$–$C_4$-alkenyl, phenyl which is unsubstituted or mono- to trisubstituted by identical or different substituents from the group consisting of fluorine, chlorine, bromine, methyl, ethyl, n- or i-propyl, n-, i-, s- or t-butyl; methoxy, ethoxy, methylthio, trifluoromethyl, trifluoromethoxy, trifluoromethylthio, cyano, nitro, dimethylamino, diethylamino, methoxycarbonyl, ethoxycarbonyl, phenyl, halogenophenyl, benzyloxy, halogenobenzyloxy, and —$NR^{12}R^{13}$, $R^{12}$ represents hydrogen, methyl, ethyl, n- or 1-propyl, n-, i, s- or t-butyl, allyl, propargyl, trifluoromethyl or represents benzyl which Is unsubstituted or mono- to trisubstituted, in the phenyl moiety, by identical or different substituents from the group consisting, of fluorine, chlorine, bromine, methyl, ethyl, n- or i-propyl, n-, i-, s- or t-butyl; methoxy, ethoxy, methylthio, trifluoromethyl, trifluoromethoxy, trifluoromethylthio, cyano, nitro, dimethylamino, diethylamino, methoxycarbonyl and ethoxycarbonyl, $R^{13}$ represents methyl, ethyl, n- or i-propyl, n-, i-, s or t-butyl, methylcarbonyl, ethylcarbonyl, methoxycarbonyl, ethoxycarbonyl, represents phenyl, phenylcarbonyl or benzyl, each of which is unsubstituted or mono- or disubstituted, in the phenyl moiety, by identical or different substituents from the group consisting of fluorine, chlorine, bromine, methyl, ethyl, n- or i-propyl, n-, i-, s- or t-butyl; methoxy, ethoxy, methylthio, trifluoromethyl, trifluoromethoxy, trifluoromethylthio, cyano, nitro, dimethylamino, diethylamino, methoxycarbonyl and ethoxycarbonyl, or represents —$CONR^{14}R^{15}$ or —$SO_2NR^{14}R^{15}$, $R^{14}$ represents hydrogen, methyl, ethyl, n- or i-propyl, n-, i-, s- or t-butyl, allyl, propargyl, trifluoromethyl or represent benzyl which is unsubstituted or mono- or di-substituted, in the phenyl moiety, by identical or different substituents from the group consisting of fluorine, chlorine, bromine, methyl, ethyl, n- or i-propyl, n-, i-, 3- or t-butyl; methoxy, ethoxy, methylthio, trifluoromethyl, trifluoromethoxy, trifluoromethylthio, cyano, nitro, dimethylamino, diethylamino, methoxycarbonyl and ethoxycarbonyl, $R^{15}$ represents methyl, ethyl, n- or i-propyl, n-, i-, s- or t-butyl, methylcarbonyl, ethylcarbonyl, methoxycarbonyl, ethoxycarbonyl, or represents phenyl, phenylcarbonyl or benzyl, each of which is unsubstituted or mono- or disubstituted, in the phenyl moiety, by identical or different substituents from the group consisting of fluorine, chlorine, bromine, methyl, ethyl, n- or i-propyl, n-, i-, s- or t-butyl-i methoxy, ethoxy, methylthio, trifluoromethyl, trifluoromethoxy, trifluoromethylthio, cyano, nitro, dimethylamino, diethylamino, methoxycarbonyl and ethoxycarbonyl, $R^5$ represents hydrogen, methyl, ethyl, n- or i-propyl, n-, i-, s- or t-butyl, allyl, propargyl, trifluoromethyl or represents benzyl which is unsubstituted or mono- or disubstituted, in the phenyl moiety, by identical or different substituents from the group consisting of fluorine, chlorine, bromine, methyl, ethyl, n- or i-propyl, n-, i-, s- or t-butyl; methoxy, ethoxy, methylthio, trifluoromethyl, trifluoromethoxy, trifluoromethylthio, cyano, nitro, dimethylamino, diethylamino, methoxycarbonyl and ethoxycarbonyl, $R^6$ represents hydrogen, methyl, ethyl, n- or i-propyl, n-, i-, s- or t-butyl, allyl, propargyl, trifluoromethyl or represents benzyl which is unsubstituted or mono- or disubstituted, in the phenyl moiety, by identical or different substituents from the group consisting of fluorine, chlorine, bromine, methyl, ethyl, n- or i-propyl, n, i-, s- or t-butyl, methoxy, ethoxy, methylthio, trifluoromethyl, trifluoromethoxy, trifluoromethylthio, cyano, nitro, dimethylamino, diethylamino, methoxycarbonyl and ethoxycarbonyl, $R^7$ represents methyl, ethyl, n- or i-propyl, n-, i-, s- or t-butyl, methylcarbonyl, ethylcarbonyl, methoxycarbonyl, ethoxy carbonyl, or represents phenyl, phenylcarbonyl or benzyl, each of which is unsubstituted or mono- or disubstituted, in the phenyl moiety, by identical or different substituents from the group consisting of fluorine, chlorine, bromine, methyl, ethyl, n- or i-propyl, n-, i-, s- or t-butyl, methoxy, ethoxy, methylthio, trifluoromethyl, trifluoromethoxy, trifluoromethylthio, cyano, nitro, dimethylamino, diethylamino, methoxy carbonyl and ethoxycarbonyl, or represents $—CONR^8R^9$ or $—SO_2NR^8R^9$, $R^8$ represents hydrogen, methyl, ethyl, n- or i-propyl, n-, i-, s, or t-butyl, allyl, propargyl, trifluoromethyl or represents benzyl which is unsubstituted or mono- to trisubstituted, in the phenyl moiety, by identical or different substituents from the group consisting of fluorine, chlorine, bromine, methyl, ethyl, n- or i-propyl, n-, i-, s- or t-butyl; methoxy, ethoxy, methylthio, trifluoromethyl, trifluoromethoxy, trifluoromethylthio, cyano, nitro, dimethylamino, diethylamino, methoxycarbonyl and ethoxycarbonyl, and $R^9$ represents methyl, ethyl, n- or i-propyl, n-, i-, s- or t-butyl, methylcarbonyl, ethylcarbonyl, methoxycarbonyl, ethoxycarbonyl, or represents phenyl, phenylcarbonyl or benzyl, each of which is unsubstituted or mono- to disubstituted, In the phenyl moiety, by identical or different substituents from the group consisting of fluorine, chlorine, bromine, methyl, ethyl, n- or i-propyl, n-, i-, s- or t-butyl; methoxy, ethoxy, methylthio, trifluoromethyl, trifluoromethoxy, trifluoromethylthio, cyano, nitro, dimethylamino, diethylamino, methoxycarbonyl and ethoxycarbonyl.

4. A compound of the formula (I) according to claim 1 wherein $X^1$ represents fluorine, chlorine, $C_1–C_2$-alkyl, $C_1–C_2$-alkoxy or $C_1–C_2$-alkylthio, $X^2$ represents hydrogen, fluorine or chlorine, $X^3$ represents hydrogen, fluorine, chlorine or $C_1–C_2$-alkyl, $R^1$ represents the radical $—OR^3$ and $R^2$ represents the radical $—OR^4$ wherein $R^3$ and $R^4$ join with the oxygen atoms to which they are attached and the carbon atom linking these to form a five-membered ring which is unsubstituted or substituted by $C_1–C_{18}$-alkyl or by phenyl which is unsubstituted or mono- or trisubstituted by identical or different substituents from the group consisting of halogen, $C_1–C_4$-alkyl, $C_1–C_4$-alkoxy, $C_1–C_4$-alkylthio, $C_1–C_4$-halogenoalkyl, $C_1–C_4$-halogenoalkoxy and $C_1–C_4$-halogenoalkylthio.

5. A compound of the formula (I) according to claim 1 wherein $X^1$, $X^2$, $X^3$, $R^1$, and $R^2$, are each as defined in the table below:

| No. | $X^1$ | $X^2$ | $X^3$ | $R^1$ | $R^2$ |
|---|---|---|---|---|---|
| 19 | F | 6-F | H | $OC_4H_9$ | $OC_4H_9$ |
| 26 | F | 6-F | H | 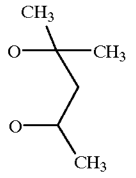 | |
| 31 | F | 6-F | H | 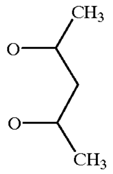 | |
| 35 | F | 6-F | H | 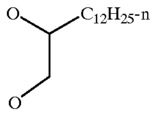 | |
| 39 | F | 6-F | H | 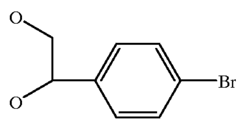 | |
| 42 | F | 6-F | H | 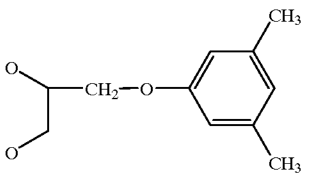 | |

-continued

| No. | $X^1$ | $X^2$ | $X^3$ | $R^1$ | $R^2$ |
|---|---|---|---|---|---|
| 43 | F | 6-F | H | 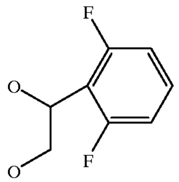 | |
| 45 | F | 6-F | H | 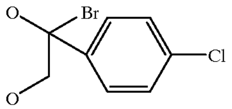 | |
| 46 | F | 6-F | H | 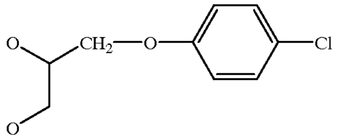 | |
| 47 | F | 6-F | H | 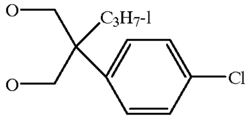 | |
| 53 | F | 6-F | H | 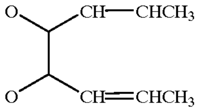 | |
| 58 | F | 6-F | H | 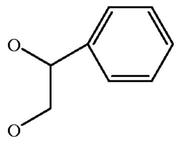 | |

6. A pesticide composition comprising at least one compound of the formula (I) according to claim 1.

7. A method for controlling pests, comprising the step of applying a compound the formula (I) according to claim 1 on pests and/or their habitat.

8. A process for preparing a pesticide, comprising the step of mixing a compound of the formula (l) according to claim 1 with extenders and/or surfactants.

9. A process for preparing a compound of the formula (I) according to claim 1, comprising the step of cyclizing a chloroethane derivative of the formula (II) wherein (II)

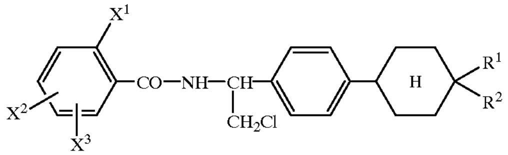

wherein $X^1$, $X^2$, $X^3$, $R^1$ and $R^2$ are each as defined in claim 1, in the presence of a base.

10. The process of claim 9 wherein the reaction is carried out in the presence of a catalyst.

11. The process of claim 9 wherein the reaction is carried out in the presence of a diluent.

12. The process of claim 9 wherein the reaction is carried out in the presence of a catalyst and a diluent.

13. A process for preparing a ketal comprising the step of reacting a 4-cyclohexylphenyl-oxazoline of the formula (Ia)

(Ia)

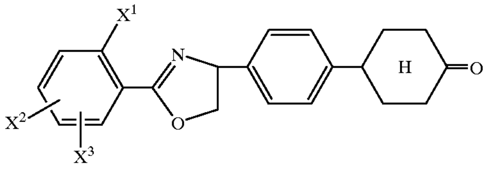

wherein $X^1$, $X^2$ and $X^3$ are each as defined in claim 1, with a compound selected from the group consisting of:

a) act alcohol of the formula (III)

$$HOR^{10} \quad (III),$$

b) a thioalcohol of the formula (IV)

$$HSR^{10} \quad (IV),$$

and c) a compound of the formula (V)

$$HO—A—O(S)H \quad (V)$$

wherein $R^{10}$ has the meanings of $R^3$ and $R^4$ in claim 1, and

A represents an unsubstituted or substituted $C_2$ or $C_3$-hydrocarbon chain.

14. The process of claim 13 wherein the reaction is carried out in the presence of a catalyst.

15. The process of claim 13 wherein the reaction is carried out in the presence of a diluent.

16. The process of claim 13 wherein the reaction is carried out in the presence of a catalyst and a diluent.

17. A process for preparing an oxime or an oxime ether comprising the step of reacting a 4-cyclohexylphenyl-oxazoline of the formula (Ia)

(Ia)

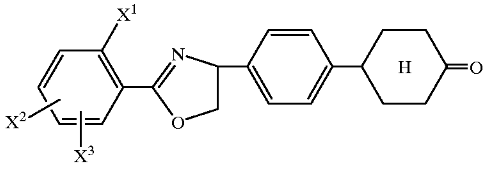

wherein $X^1$, $X^1$ and $X^3$ are each as defined in claim 1, with a hydroxylamine of the formula (VI)

$$H_2N—O—R \quad (VI)$$

wherein $R^5$ is as defined in claim 1, or salts thereof.

18. The process of claim 17 wherein the reaction is carried out in the presence of a diluent.

19. The process of claim 17 wherein the reaction is carried out in the presence of a base.

20. The process of claim 17 wherein the reaction is carried out in the presence of a diluent and a base.

21. The process of claim 17 further comprising the step of alkylating the ketal wherein $R^5$ represents hydrogen.

22. A process for preparing a hydrazone comprising the step of reacting a 4-cyclohexylphenyl-oxazoline of the formula (Ia)

(Ia)

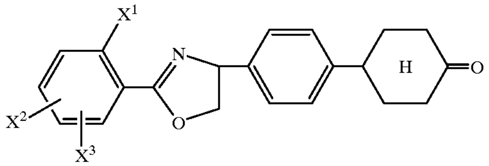

wherein $X^1$, $X^2$ and $X^3$ are each as defined in claim 1, with a hydrazine of the formula (VII)

$$H_2N—NR^6R^7 \quad (VII)$$

wherein $R^6$ and $R^7$ are as defined in claim 1.

23. The process of claim 22 wherein the reaction is carried out in the presence of a diluent.

24. A process for preparing a 4-cyclohexylphenyl-oxazoline of the formula (Ic)

(Ic)

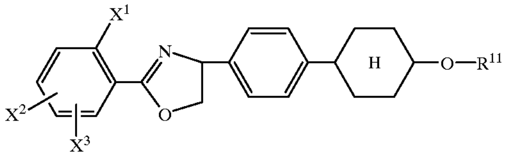

comprising the step of reacting a 4-cyclohexylphenyl-oxazoline of the formula (Ib)

(Ib)

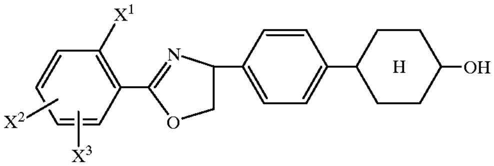

wherein $X^1$, $X^2$ and $X^3$ are each as defined in claim 1, with a halide of the formula (VIII)

$$R^{11}—Hal \quad (VIII)$$

wherein $R^{11}$ represents alkyl or unsubstituted or substituted benzyl, and

Hal represents halogen, in the presence of a base.

25. The process of claim 24 wherein tho reaction is carried out in the presence of a diluent.

* * * * *